United States Patent
Jones et al.

(10) Patent No.: US 7,456,257 B2
(45) Date of Patent: Nov. 25, 2008

(54) FUSION PROTEINS OF INTERFERON ALPHA MUTEINS WITH IMPROVED PROPERTIES

(75) Inventors: Tim Jones, Babraham (GB); Matthew Baker, Horningsea (GB); Marian Hanlon, Cambridge (GB); Francis Joseph Carr, Balmedie (GB)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/546,112

(22) PCT Filed: Feb. 18, 2004

(86) PCT No.: PCT/EP2004/001524

§ 371 (c)(1),
(2), (4) Date: Oct. 27, 2006

(87) PCT Pub. No.: WO2004/074486

PCT Pub. Date: Sep. 2, 2004

(65) Prior Publication Data

US 2007/0148739 A1    Jun. 28, 2007

(30) Foreign Application Priority Data

Feb. 18, 2003    (EP)    .................................. 03003647

(51) Int. Cl.
*C07K 14/00*    (2006.01)
(52) U.S. Cl. ...................................................... 530/351
(58) Field of Classification Search ................... 530/350; 514/2; 536/23.1
See application file for complete search history.

(56) References Cited

U.S. PATENT DOCUMENTS

2002/0081664 A1 *    6/2002    Lo et al. ..................... 435/69.5

FOREIGN PATENT DOCUMENTS

WO    WO 02/085941    * 10/2002

* cited by examiner

*Primary Examiner*—Karen Cochrane Carlson
(74) *Attorney, Agent, or Firm*—Olson & Cepuritis, Ltd.

(57) ABSTRACT

The invention concerns human interferon alpha and in particular modified forms of interferon alpha 2 with improved properties. The improved proteins contain amino acid substitutions at specific positions that confer increased relative activity in biological assays. The invention provides also modified interferon alpha with improved biological activity concomitant with reduced immunogenic potential in the protein. The improved proteins are intended for therapeutic use in the treatment of diseases in humans.

1 Claim, 18 Drawing Sheets

FIGURE 1

| Mutant | Wt IFN IFN5 | IFN28 | IFN64 | IFN164 | IFN167 | IFN168 | IFN171 | IFN172 | IFN173 | IFN174 | IFN176 | IFN197 | IFN201 | IFN202 | IFN219 | IFN248 | IFN270 | IFN273 | IFN276 | IFN306 | IFN311 | IFN315* |
|---|---|---|---|---|---|---|---|---|---|---|---|---|---|---|---|---|---|---|---|---|---|---|
| IFN AA No. | | | | | | | | | | | | | | | | | | | | | | |
| 24 | I | | | | | | | | | | | | | | | | | | | | | |
| 57 | H | | | | | | | | | | | | | | Y | | | | | Q | Q | Q |
| 60 | I | | | | | | | | T | T | | | | | | | | | | | | |
| 64 | F | | | | | | | | | | | | | | T | T | T | T | T | | T | T |
| 76 | W | | H | | | | | | | H | H | H | H | H | H | A | A | A | A | | A | A |
| 89 | Y | D | | | | | | | | | | N | | | | H | H | H | H | H | H | H |
| 116 | I | | | D | H | N | S | | | | | | | | | | | | | | | |
| 128 | L | | | | | | | T | T | T | T | | T | P | | | N | R | T | | R | R |
| 156 | N | | | | | | | | S | S | S | | | | | | N | N | N | | N | N |
| Signaling assay Relative activity | 1 | 10 | >3 | 3 | 2 | 2 | 4 | 7 | 10 | 5 | 5 | 2 | 7 | 5 | 17 | 1 | 2 | 3 | 3 | 4 | >1,30 | >9 |
| Anti-viral Relative activity | 1 | ND | ND | ND | ND | ND | ND | ND | ND | ND | ND | ND | ND | ND | ND | 2.8 | 6.3 | 4.6 | 4.6 | 2 | 7.4 | 36 |
| | | | | | | | | | | | | | | | | | | | Anti-proliferation Relative activity | 1 | 1 | 1 |

IFN5:

```
         10         20         30         40         50
EPKSSDKTHT CPPCPAPELL GGPSVFLFPP KPKDTLMISR TPEVTCVVVD 60         70         80         90        100
VSHEDPEVKF NWYVDGVEVH NAKTKPREEQ YNSTYRVVSV LTVLHQDWLN 110        120        130        140        150
GKEYKCKVSN KALPAPIEKT ISKAKGQPRE PQVYTLPPSR EEMTKNQVSL 160        170        180        190        200
TCLVKGFYPS DIAVEWESNG QPENNYKTTP PVLDSDGSFF YSKLTVDKSR 210        220        230        240        250
WQQGNVFSCS VMHEALHNHY TQKSLSLSPG KCDLPQTHSL GSRRTLMLLA 260        270        280        290        300
QMRRISLFSC LKDRHDFGFP QEEFGNQFQK AETIPVLHEM IQQIFNLFST 310        320        330        340        350
KDSSAAWDET LLDKFYTELY QQLNDLEACV IQGVGVTETP LMKEDSILAV 360        370        380        390
RKYFQRITLY LKEKKYSPCA WEVVRAEIMR SFSLSTNLQE SLRSKE
```

IFN28:

```
         10         20         30         40         50
EPKSSDKTHT CPPCPAPELL GGPSVFLFPP KPKDTLMISR TPEVTCVVVD 60         70         80         90        100
VSHEDPEVKF NWYVDGVEVH NAKTKPREEQ YNSTYRVVSV LTVLHQDWLN 110        120        130        140        150
GKEYKCKVSN KALPAPIEKT ISKAKGQPRE PQVYTLPPSR EEMTKNQVSL 160        170        180        190        200
TCLVKGFYPS DIAVEWESNG QPENNYKTTP PVLDSDGSFF YSKLTVDKSR 210        220        230        240        250
WQQGNVFSCS VMHEALHNHY TQKSLSLSPG KCDLPQTHSL GSRRTLMLLA 260        270        280        290        300
QMRRISLFSC LKDRHDFGFP QEEFGNQFQK AETIPVLHEM IQQIFNLFST 310        320        330        340        350
KDSSAAWDET LLDKFYTELD QQLNDLEACV IQGVGVTETP LMKEDSILAV 360        370        380        390
RKYFQRITLY LKEKKYSPCA WEVVRAEIMR SFSLSTNLQE SLRSKE
```

FIGURE 5.2

IFN64:

```
         10         20         30         40         50
EPKSSDKTHT CPPCPAPELL GGPSVFLFPP KPKDTLMISR TPEVTCVVVD
         60         70         80         90        100
VSHEDPEVKF NWYVDGVEVH NAKTKPREEQ YNSTYRVVSV LTVLHQDWLN
        110        120        130        140        150
GKEYKCKVSN KALPAPIEKT ISKAKGQPRE PQVYTLPPSR EEMTKNQVSL
        160        170        180        190        200
TCLVKGFYPS DIAVEWESNG QPENNYKTTP PVLDSDGSFF YSKLTVDKSR
        210        220        230        240        250
WQQGNVFSCS VMHEALHNHY TQKSLSLSPG KCDLPQTHSL GSRRTLMLLA
        260        270        280        290        300
QMRRISLFSC LKDRHDFGFP QEEFGNQFQK AETIPVLHEM IQQIFNLFST
        310        320        330        340        350
KDSSAAHDET LLDKFYTELY QQLNDLEACV IQGVGVTETP LMKEDSILAV
        360        370        380        390
RKYFQRITLY LKEKKYSPCA WEVVRAEIMR SFSLSTNLQE SLRSKE
```

IFN164:

```
         10         20         30         40         50
EPKSSDKTHT CPPCPAPELL GGPSVFLFPP KPKDTLMISR TPEVTCVVVD
         60         70         80         90        100
VSHEDPEVKF NWYVDGVEVH NAKTKPREEQ YNSTYRVVSV LTVLHQDWLN
        110        120        130        140        150
GKEYKCKVSN KALPAPIEKT ISKAKGQPRE PQVYTLPPSR EEMTKNQVSL
        160        170        180        190        200
TCLVKGFYPS DIAVEWESNG QPENNYKTTP PVLDSDGSFF YSKLTVDKSR
        210        220        230        240        250
WQQGNVFSCS VMHEALHNHY TQKSLSLSPG KCDLPQTHSL GSRRTLMLLA
        260        270        280        290        300
QMRRISLFSC LKDRHDFGFP QEEFGNQFQK AETIPVLHEM IQQIFNLFST
        310        320        330        340        350
KDSSAAWDET LLDKFYTELY QQLNDLEACV IQGVGVTETP LMKEDSILAV
        360        370        380        390
RKYFQRITDY LKEKKYSPCA WEVVRAEIMR SFSLSTNLQE SLRSKE
```

FIGURE 5.3

IFNL67:

```
         10         20         30         40         50
EPKSSDKTHT CPPCPAPELL GGPSVFLFPP KPKDTLMISR TPEVTCVVVD
         60         70         80         90        100
VSHEDPEVKF NWYVDGVEVH NAKTKPREEQ YNSTYRVVSV LTVLHQDWLN
        110        120        130        140        150
GKEYKCKVSN KALPAPIEKT ISKAKGQPRE PQVYTLPPSR EEMTKNQVSL
        160        170        180        190        200
TCLVKGFYPS DIAVEWESNG QPENNYKTTP PVLDSDGSFF YSKLTVDKSR
        210        220        230        240        250
WQQGNVFSCS VMHEALHNHY TQKSLSLSPG KCDLPQTHSL GSRRTLMLLA
        260        270        280        290        300
QMRRISLFSC LKDRHDFGFP QEEFGNQFQK AETIPVLHEM IQQIFNLFST
        310        320        330        340        350
KDSSAAWDET LLDKFYTELY QQLNDLEACV IQGVGVTETP LMKEDSILAV
        360        370        380        390
RKYFQRITHY LKEKKYSPCA WEVVRAEIMR SFSLSTNLQE SLRSKE
```

IFNL68:

```
         10         20         30         40         50
EPKSSDKTHT CPPCPAPELL GGPSVFLFPP KPKDTLMISR TPEVTCVVVD
         60         70         80         90        100
VSHEDPEVKF NWYVDGVEVH NAKTKPREEQ YNSTYRVVSV LTVLHQDWLN
        110        120        130        140        150
GKEYKCKVSN KALPAPIEKT ISKAKGQPRE PQVYTLPPSR EEMTKNQVSL
        160        170        180        190        200
TCLVKGFYPS DIAVEWESNG QPENNYKTTP PVLDSDGSFF YSKLTVDKSR
        210        220        230        240        250
WQQGNVFSCS VMHEALHNHY TQKSLSLSPG KCDLPQTHSL GSRRTLMLLA
        260        270        280        290        300
QMRRISLFSC LKDRHDFGFP QEEFGNQFQK AETIPVLHEM IQQIFNLFST
        310        320        330        340        350
KDSSAAWDET LLDKFYTELY QQLNDLEACV IQGVGVTETP LMKEDSILAV
        360        370        380        390
RKYFQRITNY LKEKKYSPCA WEVVRAEIMR SFSLSTNLQE SLRSKE
```

FIGURE 5.4

IFN171:

```
         10         20         30         40         50
EPKSSDKTHT CPPCPAPELL GGPSVFLFPP KPKDTLMISR TPEVTCVVVD
         60         70         80         90        100
VSHEDPEVKF NWYVDGVEVH NAKTKPREEQ YNSTYRVVSV LTVLHQDWLN
        110        120        130        140        150
GKEYKCKVSN KALPAPIEKT ISKAKGQPRE PQVYTLPPSR EEMTKNQVSL
        160        170        180        190        200
TCLVKGFYPS DIAVEWESNG QPENNYKTTP PVLDSDGSFF YSKLTVDKSR
        210        220        230        240        250
WQQGNVFSCS VMHEALHNHY TQKSLSLSPG KCDLPQTHSL GSRRTIMLLA
        260        270        280        290        300
QMRRISLFSC LKDRHDFGFP QEEFGNQFQK AETIPVLHEM IQQIFNLFST
        310        320        330        340        350
KDSSAAWDET LLDKFYTELY QQLNDLEACV IQGVGVTETP LMKEDSILAV
        360        370        380        390
RKYFQRITSY LKEKKYSPCA WEVVRAEIMR SFSLSTNLQE SLRSKE
```

IFN172:

```
         10         20         30         40         50
EPKSSDKTHT CPPCPAPELL GGPSVFLFPP KPKDTLMISR TPEVTCVVVD
         60         70         80         90        100
VSHEDPEVKF NWYVDGVEVH NAKTKPREEQ YNSTYRVVSV LTVLHQDWLN
        110        120        130        140        150
GKEYKCKVSN KALPAPIEKT ISKAKGQPRE PQVYTLPPSR EEMTKNQVSL
        160        170        180        190        200
TCLVKGFYPS DIAVEWESNG QPENNYKTTP PVLDSDGSFF YSKLTVDKSR
        210        220        230        240        250
WQQGNVFSCS VMHEALHNHY TQKSLSLSPG KCDLPQTHSL GSRRTIMLLA
        260        270        280        290        300
QMRRISLFSC LKDRHDFGFP QEEFGNQFQK AETIPVLHEM IQQIFNLFST
        310        320        330        340        350
KDSSAAWDET LLDKFYTELY QQLNDLEACV IQGVGVTETP LMKEDSILAV
        360        370        380        390
RKYFQRITTY LKEKKYSPCA WEVVRAEIMR SFSLSTNLQE SLRSKE
```

FIGURE 5.5

IFN173:

```
         10         20         30         40         50
EPKSSDKTHT CPPCPAPELL GGPSVFLFPP KPKDTLMISR TPEVTCVVVD
         60         70         80         90        100
VSHEDPEVKF NWYVDGVEVH NAKTKPREEQ YNSTYRVVSV LTVLHQDWLN
        110        120        130        140        150
GKEYKCKVSN KALPAPIEKT ISKAKGQPRE PQVYTLPPSR EEMTKNQVSL
        160        170        180        190        200
TCLVKGFYPS DIAVEWESNG QPENNYKTTP PVLDSDGSFF YSKLTVDKSR
        210        220        230        240        250
WQQGNVFSCS VMHEALHNHY TQKSLSLSPG KCDLPQTHSL GSRRTLMLLA
        260        270        280        290        300
QMRRISLFSC LKDRHDFGFP QEEFGNQFQK AETIPVLHEM TQQIFNLFST
        310        320        330        340        350
KDSSAAWDET LLDKFYTELY QQLNDLEACV IQGVGVTETP LMKEDSILAV
        360        370        380        390
RKYFQRITTY LKEKKYSPCA WEVVRAEIMR SFSLSTSLQE SLRSKE
```

IFN174:

```
         10         20         30         40         50
EPKSSDKTHT CPPCPAPELL GGPSVFLFPP KPKDTLMISR TPEVTCVVVD
         60         70         80         90        100
VSHEDPEVKF NWYVDGVEVH NAKTKPREEQ YNSTYRVVSV LTVLHQDWLN
        110        120        130        140        150
GKEYKCKVSN KALPAPIEKT ISKAKGQPRE PQVYTLPPSR EEMTKNQVSL
        160        170        180        190        200
TCLVKGFYPS DIAVEWESNG QPENNYKTTP PVLDSDGSFF YSKLTVDKSR
        210        220        230        240        250
WQQGNVFSCS VMHEALHNHY TQKSLSLSPG KCDLPQTHSL GSRRTLMLLA
        260        270        280        290        300
QMRRISLFSC LKDRHDFGFP QEEFGNQFQK AETIPVLHEM TQQIFNLFST
        310        320        330        340        350
KDSSAAHDET LLDKFYTELY QQLNDLEACV IQGVGVTETP LMKEDSILAV
        360        370        380        390
RKYFQRITTY LKEKKYSPCA WEVVRAEIMR SFSLSTSLQE SLRSKE
```

FIGURE 5.6

IFN176:

```
         10          20          30          40          50
EPKSSDKTHT CPPCPAPELL GGPSVFLFPP KPKDTLMISR TPEVTCVVVD
         60          70          80          90         100
VSHEDPEVKF NWYVDGVEVH NAKTKPREEQ YNSTYRVVSV LTVLHQDWLN
        110         120         130         140         150
GKEYKCKVSN KALPAPIEKT ISKAKGQPRE PQVYTLPPSR EEMTKNQVSL
        160         170         180         190         200
TCLVKGFYPS DIAVEWESNG QPENNYKTTP PVLDSDGSFF YSKLTVDKSR
        210         220         230         240         250
WQQGNVFSCS VMHEALHNHY TQKSLSLSPG KCDLPQTHSL GSRRTLMLLA
        260         270         280         290         300
QMRRISLFSC LKDRHDFGFP QEEFGNQFQK AETIPVLHEM IQQIFNLFST
        310         320         330         340         350
KDSSAAHDET LLDKFYTELY QQLNDLEACV IQGVGVTETP LMKEDSILAV
        360         370         380         390
RKYFQRITTY LKEKKYSPCA WEVVRAEIMR SFSLSTSIQE SLRSKE
```

IFN197:

```
         10          20          30          40          50
EPKSSDKTHT CPPCPAPELL GGPSVFLFPP KPKDTLMISR TPEVTCVVVD
         60          70          80          90         100
VSHEDPEVKF NWYVDGVEVH NAKTKPREEQ YNSTYRVVSV LTVLHQDWLN
        110         120         130         140         150
GKEYKCKVSN KALPAPIEKT ISKAKGQPRE PQVYTLPPSR EEMTKNQVSL
        160         170         180         190         200
TCLVKGFYPS DIAVEWESNG QPENNYKTTP PVLDSDGSFF YSKLTVDKSR
        210         220         230         240         250
WQQGNVFSCS VMHEALHNHY TQKSLSLSPG KCDLPQTHSL GSRRTLMLLA
        260         270         280         290         300
QMRRISLFSC LKDRHDFGFP QEEFGNQFQK AETIPVLHEM IQQIFNLFST
        310         320         330         340         350
KDSSAAHDET LLDKFYTELY QQLNDLEACV IQGVGVTETP LMKEDSNLAV
        360         370         380         390
RKYFQRITLY LKEKKYSPCA WEVVRAEIMR SFSLSTNLQE SLRSKE
```

FIGURE 5.7

IFN201:

```
         10         20         30         40         50
EPKSSDKTHT CPPCPAPELL GGPSVFLFPP KPKDTLMISR TPEVTCVVVD
         60         70         80         90        100
VSHEDPEVKF NWYVDGVEVH NAKTKPREEQ YNSTYRVVSV LTVLHQDWLN
        110        120        130        140        150
GKEYKCKVSN KALPAPIEKT ISKAKGQPRE PQVYTLPPSR EEMTKNQVSL
        160        170        180        190        200
TCLVKGFYPS DIAVEWESNG QPENNYKTTP PVLDSDGSFF YSKLTVDKSR
        210        220        230        240        250
WQQGNVFSCS VMHEALHNHY TQKSLSLSPG KCDLPQTHSL GSRRTLMLLA
        260        270        280        290        300
QMRRISLFSC LKDRHDFGFP QEEFGNQFQK AETIPVLHEM IQQIFNLFST
        310        320        330        340        350
KDSSAAHDET LLDKFYTELY QQLNDLEACV IQGVGVTETP LMKEDSTLAV
        360        370        380        390
RKYFQRITLY LKEKKYSPCA WEVVRAEIMR SFSLSTNLQE SLRSKE
```

IFN202:

```
         10         20         30         40         50
EPKSSDKTHT CPPCPAPELL GGPSVFLFPP KPKDTLMISR TPEVTCVVVD
         60         70         80         90        100
VSHEDPEVKF NWYVDGVEVH NAKTKPREEQ YNSTYRVVSV LTVLHQDWLN
        110        120        130        140        150
GKEYKCKVSN KALPAPIEKT ISKAKGQPRE PQVYTLPPSR EEMTKNQVSL
        160        170        180        190        200
TCLVKGFYPS DIAVEWESNG QPENNYKTTP PVLDSDGSFF YSKLTVDKSR
        210        220        230        240        250
WQQGNVFSCS VMHEALHNHY TQKSLSLSPG KCDLPQTHSL GSRRTLMLLA
        260        270        280        290        300
QMRRISLFSC LKDRHDFGFP QEEFGNQFQK AETIPVLHEM IQQIFNLFST
        310        320        330        340        350
KDSSAAHDET LLDKFYTELY QQLNDLEACV IQGVGVTETP LMKEDSPLAV
        360        370        380        390
RKYFQRITLY LKEKKYSPCA WEVVRAEIMR SFSLSTNLQE SLRSKE
```

FIGURE 5.8

IFN219:

```
         10          20          30          40          50
EPKSSDKTHT CPPCPAPELL GGPSVFLFPP KPKDTLMISR TPEVTCVVVD
         60          70          80          90         100
VSHEDPEVKF NWYVDGVEVH NAKTKPREEQ YNSTYRVVSV LTVLHQDWLN
        110         120         130         140         150
GKEYKCKVSN KALPAPIEKT ISKAKGQPRE PQVYTLPPSR EEMTKNQVSL
        160         170         180         190         200
TCLVKGFYPS DIAVEWESNG QPENNYKTTP PVLDSDGSFF YSKLTVDKSR
        210         220         230         240         250
WQQGNVFSCS VMHEALHNHY TQKSLSLSPG KCDLPQTHSL GSRRTLMLLA
        260         270         280         290         300
QMRRISLFSC LKDRHDFGFP QEEFGNQFQK AETIPVLYEM IQQITNLFST
        310         320         330         340         350
KDSSAAHDET LLDKFYTELY QQLNDLEACV IQGVGVTETP LMKEDSILAV
        360         370         380         390
RKYFQRITLY LKEKKYSPCA WEVVRAEIMR SFSLSTNLQE SLRSKE
```

IFN248:

```
         10          20          30          40          50
EPKSSDKTHT CPPCPAPELL GGPSVFLFPP KPKDTLMISR TPEVTCVVVD
         60          70          80          90         100
VSHEDPEVKF NWYVDGVEVH NAKTKPREEQ YNSTYRVVSV LTVLHQDWLN
        110         120         130         140         150
GKEYKCKVSN KALPAPIEKT ISKAKGQPRE PQVYTLPPSR EEMTKNQVSL
        160         170         180         190         200
TCLVKGFYPS DIAVEWESNG QPENNYKTTP PVLDSDGSFF YSKLTVDKSR
        210         220         230         240         250
WQQGNVFSCS VMHEALHNHY TQKSLSLSPG KCDLPQTHSL GSRRTLMLLA
        260         270         280         290         300
QMRRISLFSC LKDRHDFGFP QEEFGNQFQK AETIPVLHEM TQQIANLFST
        310         320         330         340         350
KDSSAAHDET LLDKFYTELY QQLNDLEACV IQGVGVTETP LMKEDSILAV
        360         370         380         390
RKYFQRITLY LKEKKYSPCA WEVVRAEIMR SFSLSTNLQE SLRSKE
```

FIGURE 5.9

IFN270:

```
         10          20          30          40          50
EPKSSDKTHT CPPCPAPELL GGPSVFLFPP KPKDTLMISR TPEVTCVVVD
         60          70          80          90         100
VSHEDPEVKF NWYVDGVEVH NAKTKPREEQ YNSTYRVVSV LTVLHQDWLN
        110         120         130         140         150
GKEYKCKVSN KALPAPIEKT ISKAKGQPRE PQVYTLPPSR EEMTKNQVSL
        160         170         180         190         200
TCLVKGFYPS DIAVEWESNG QPENNYKTTP PVLDSDGSFF YSKLTVDKSR
        210         220         230         240         250
WQQGNVFSCS VMHEALHNHY TQKSLSLSPG KCDLPQTHSL GSRRTLMLLA
        260         270         280         290         300
QMRRISLFSC LKDRHDFGFP QEEFGNQFQK AETIPVLHEM TQQIANLFST
        310         320         330         340         350
KDSSAAHDET LLDKFYTELY QQLNDLEACV IQGVGVTETP LMKEDSNLAV
        360         370         380         390
RKYFQRITNY LKEKKYSPCA WEVVRAEIMR SFSLSTNLQE SLRSKE
```

IFN273:

```
         10          20          30          40          50
EPKSSDKTHT CPPCPAPELL GGPSVFLFPP KPKDTLMISR TPEVTCVVVD
         60          70          80          90         100
VSHEDPEVKF NWYVDGVEVH NAKTKPREEQ YNSTYRVVSV LTVLHQDWLN
        110         120         130         140         150
GKEYKCKVSN KALPAPIEKT ISKAKGQPRE PQVYTLPPSR EEMTKNQVSL
        160         170         180         190         200
TCLVKGFYPS DIAVEWESNG QPENNYKTTP PVLDSDGSFF YSKLTVDKSR
        210         220         230         240         250
WQQGNVFSCS VMHEALHNHY TQKSLSLSPG KCDLPQTHSL GSRRTLMLLA
        260         270         280         290         300
QMRRISLFSC LKDRHDFGFP QEEFGNQFQK AETIPVLHEM TQQIANLFST
        310         320         330         340         350
KDSSAAHDET LLDKFYTELY QQLNDLEACV IQGVGVTETP LMKEDSRLAV
        360         370         380         390
RKYFQRITNY LKEKKYSPCA WEVVRAEIMR SFSLSTNLQE SLRSKE
```

FIGURE 5.10

IFN276:

```
         10         20         30         40         50
EPKSSDKTHT CPPCPAPELL GGPSVFLFPP KPKDTLMISR TPEVTCVVVD
         60         70         80         90        100
VSHEDPEVKF NWYVDGVEVH NAKTKPREEQ YNSTYRVVSV LTVLHQDWLN
        110        120        130        140        150
GKEYKCKVSN KALPAPIEKT ISKAKGQPRE PQVYTLPPSR EEMTKNQVSL
        160        170        180        190        200
TCLVKGFYPS DIAVEWESNG QPENNYKTTP PVLDSDGSFF YSKLTVDKSR
        210        220        230        240        250
WQQGNVFSCS VMHEALHNHY TQKSLSLSPG KCDLPQTHSL GSRRTLMLLA
        260        270        280        290        300
QMRRISLFSC LKDRHDFGFP QEEFGNQFQK AETIPVLHEM TQQIANLFST
        310        320        330        340        350
KDSSAAHDET LLDKFYTELY QQLNDLEACV IQGVGVTETP LMKEDSTLAV
        360        370        380        390
RKYFQRITNY LKEKKYSPCA WEVVRAEIMR SFSLSTNLQE SLRSKE
```

IFN306:

```
         10         20         30         40         50
EPKSSDKTHT CPPCPAPELL GGPSVFLFPP KPKDTLMISR TPEVTCVVVD
         60         70         80         90        100
VSHEDPEVKF NWYVDGVEVH NAKTKPREEQ YNSTYRVVSV LTVLHQDWLN
        110        120        130        140        150
GKEYKCKVSN KALPAPIEKT ISKAKGQPRE PQVYTLPPSR EEMTKNQVSL
        160        170        180        190        200
TCLVKGFYPS DIAVEWESNG QPENNYKTTP PVLDSDGSFF YSKLTVDKSR
        210        220        230        240        250
WQQGNVFSCS VMHEALHNHY TQKSLSLSPG KCDLPQTHSL GSRRTLMLLA
        260        270        280        290        300
QMRRQSLFSC LKDRHDFGFP QEEFGNQFQK AETIPVLHEM IQQIFNLFST
        310        320        330        340        350
KDSSAAHDET LLDKFYTELY QQLNDLEACV IQGVGVTETP LMKEDSILAV
        360        370        380        390
RKYFQRITLY LKEKKYSPCA WEVVRAEIMR SFSLSTNLQE SLRSKE
```

FIGURE 5.11

IFN311:

```
           10         20         30         40         50
  EPKSSDKTHT CPPCPAPELL GGPSVFLFPP KPKDTLMISR TPEVTCVVVD
           60         70         80         90        100
  VSHEDPEVKF NWYVDGVEVH NAKTKPREEQ YNSTYRVVSV LTVLHQDWLN
          110        120        130        140        150
  GKEYKCKVSN KALPAPIEKT ISKAKGQPRE PQVYTLPPSR EEMTKNQVSL
          160        170        180        190        200
  TCLVKGFYPS DIAVEWESNG QPENNYKTTP PVLDSDGSFF YSKLTVDKSR
          210        220        230        240        250
  WQQGNVFSCS VMHEALHNHY TQKSLSLSPG KCDLPQTHSL GSRRTLMLLA
          260        270        280        290        300
  QMRRQSLFSC LKDRHDFGFP QEEFGNQFQK AETIPVLHEM TQQIANLFST
          310        320        330        340        350
  KDSSAAHDET LLDKFYTELY QQINDLEACV IQGVGVTETP LMKEDSRLAV
          360        370        380        390
  RKYFQRITNY LKEKKYSPCA WEVVRAEIMR SFSLSTNLQE SLRSKE
```

IFN316:

```
           10         20         30         40         50
  EPKSSDKTHT CPPCPAPELL GGPSVFLFPP KPKDTLMISR TPEVTCVVVD
           60         70         80         90        100
  VSHEDPEVKF NWYVDGVEVH NAKTKPREEQ YNSTYRVVSV LTVLHQDWLN
          110        120        130        140        150
  GKEYKCKVSN KALPAPIEKT ISKAKGQPRE PQVYTLPPSR EEMTKNQVSL
          160        170        180        190        200
  TCLVKGFYPS DIAVEWESNG QPENNYKTTP PVLDSDGSFF YSKLTVDKSR
          210        220        230        240        250
  WQQGNVFSCS VMHEALHNHY TQKSLSLSPG AGGGGSGGGG SGGGSGCDLP
          260        270        280        290        300
  QTHSLGSRRT LMLLAQMRRQ SLFSCLKDRH DFGFPQEEFG NQFQKAETIP
          310        320        330        340        350
  VLHEMTQQIA NLFSTKDSSA AHDETLLDKF YTELYQQIND LEACVIQGVG
          360        370        380        390        400
  VTETPLMKED SRLAVRKYFQ RITNYLKEKK YSPCAWEVVR AEIMRSFSLS
          410
  TNLQESLRSK E
```

FIGURE 5.12

IFN120:

```
         10         20         30         40         50
EPKSSDKTHT CPPCPAPELL GGPSVFLFPP KPKDTLMISR TPEVTCVVVD
         60         70         80         90        100
VSHEDPEVKF NWYVDGVEVH NAKTKPREEQ YNSTYRVVSV LTVLHQDWLN
        110        120        130        140        150
GKEYKCKVSN KALPAPIEKT ISKAKGQPRE PQVYTLPPSR EEMTKNQVSL
        160        170        180        190        200
TCLVKGFYPS DIAVEWESNG QPENNYKTTP PVLDSDGSFF YSKLTVDKSR
        210        220        230        240        250
WQQGNVFSCS VMHEALHNHY TQKSLSLSPG AGGGGSGGGG SGGGGSGCDLP
        260        270        280        290        300
QTHSLGSRRT LMLLAQMRRI SLFSCLKDRH DFGFPQEEFG NQFQKAETIP
        310        320        330        340        350
VLHEMIQQIF NLFSTKDSSA AWDETLLDKF YTELYQQLND LEACVIQGVG
        360        370        380        390        400
VIETPLMKED SILAVRKYFQ RITLYLKEKK YSPCAWEVVR AEIMRSFSLS
        410
TNLQESLRSK E
```

FUSION PROTEINS OF INTERFERON ALPHA MUTEINS WITH IMPROVED PROPERTIES

This application is the National Stage of International Application No. PCT/EP2004/001524, filed on Feb. 18, 2004.

FIELD

The invention concerns human interferon alpha and in particular modified forms of interferon alpha 2 with improved properties. The improved proteins contain amino acid substitutions at specific positions that confer increased relative activity in biological assays. The invention provides also modified interferon alpha with improved biological activity concomitant with reduced immunogenic potential in the protein. The improved proteins are intended for therapeutic use in the treatment of diseases in humans.

BACKGROUND

Interferon alpha 2 (IFNα2) is an important glycoprotein cytokine expressed by activated macrophages. The protein has considerable clinical importance as a broad spectrum anti-viral, anti-proliferative and immunomodulating agent. Recombinant and other preparations of INFα2 have been used therapeutically in a variety of cancer and anti-viral indications in man [reviewed in Sen, G. G. and Lengyel P, (1992), *J. Biol. Chem.* 267: 5017-5020]. Currently there are a number of IFNα preparations in clinical use, including native recombinant IFNα2s produced in *E. coli* (IFNα2a, RoferonA®, Hoffman-La Roche; IFNα2b, IntronA®, Schering-Plough; IFNα2c, Berofor®, Basotherm) and more recently a synthetic IFNα, also produced in *E. coli*, based upon the consensus sequence of all subtypes (Infergen®, InterMune).

A major use of IFNα2 is the treatment of chronic hepatitis C virus (HCV) infection. Treatment with IFNα alone results in sustained virus clearance in around 10% of patients, although more recently sustained viral responses of 40% have been achieved with the combination of IFNα2 with ribavirin [Davis G L, et al, (1998) *N. Engl. J. Med.;* 339:1493-1499; McHutchison J G et al (1998) *N. Engl. J Med.;* 339:1485-1492; Reichard O, et al (1998) *Lancet.* 351:83-87]. IFNα therapy is intensive and associated with severe side effects leading to withdrawal of treatment in up to 20% of cases. The rationale for intensive therapy is that IFNα2b has a relatively short serum half-life [Glue P, et al (2000) *Clin. Pharmacol. Ther.;* 68:556-567], requiring administration by subcutaneous injection once daily or three times weekly for anti-viral efficacy.

The short half-life and frequent dosing have been recognised as problematic in long-term treatment. To address this 'pegylated' versions of RoferonA® and IntronA® (Pegasys® and Peg-Intron®) have been introduced and a similar version of Infergen® is in phase II clinical trials. These modified interferons are conjugated to polyethylene glycol moieties which increases the serum half-life 10 to 20 fold (6,7), thereby reducing the dosing frequency to once weekly (180 μg or 1.4 μg/Kg for Peg-Intron™ and Pegasys™ respectively) without adversely affecting clinical efficacy [Glue P. et al (2000) ibid; Perry C M, et al (2001) *Drugs;* 61:2263-2288; Glue P, et al (2000) *Hepatology;* 32:647-653]. In these studies, the side effect profiles are similar to unmodified interferon.

Another strategy for increasing serum half-life is to link IFNα to human serum albumin [Osborn B L, et al (2002) *J. Pharmacol. Exp. Ther.;* 303:540-548]. Albuferon® consists of IFNα linked to the C-terminus of human serum albumin and, in cynomolgus monkeys, has a half-life 3 fold greater than that of pegylated IFNα and 18 fold greater than unmodified IFNα. Data from studies in humans are not yet available for this molecule. However for both pegylated and albumin linked IFNα, the in vitro specific activity of the modified proteins is reduced compared to native protein, to 28% with Peg-Intron® [Grace M, et al. (2001) *Cytokine Res.;* 21:1103-1115] and to 10% or less with Pegasys® and Albuferon® [Osborn B L, et al (2002) ibid; Bailon P, et al (2001). *Bioconjug Chem.* 12:195-202].

Despite the significant therapeutic benefit found in using IFNα, resistance to therapy in certain patients has been documented and one important mechanism of resistance has been shown to be the development of neutralising antibodies detectable in the serum of treated patients [Quesada, J. R. et al (1985) *J. Clin. Oncology* 3:1522-1528; Stein R. G. et al (1988) ibid; Russo, D. et al (1996) *Br. J. Haematol.;* 94:300-305; Brooks M. G. et al (1989) *Gut* 30: 1116-1122]. An immune response in these patients is mounted to the therapeutic interferon despite the fact that a molecule of at least identical primary structure is produced endogenously in man Repeated dosing over several months induces anti-IFNα neutralising antibodies in up to 80% of patients, depending upon the indication [Schellekens H, et al (1997) *J Interfron Cytokine Res.* 17 Suppl 1:S5-8], with the reported frequency for chronic HCV infection ranging from 7% to 60% [Schellekens H, et al (1997) ibid]. Available evidence suggests that patients who develop neutralising antibodies are more likely to fail to respond to treatment and suffer relapse than those who do not develop antibodies [Ross C, et al (2002) *J Interferon Cytokine Res.;* 22: 421-426; McKenna R. M, et al (1997) *J. Interferon Cytokine Res.;* 17:141-143; Russo D, et al (1996) ibid; Milella M, et al (1993) *Liver;* 13:146-150; Primmer O. (1993) *Cancer;* 71:1828-1834], although in some cases treatment can be rescued by the subsequent use of purified leukocyte interferon [Russo D, et al (1996) ibid; Oberg K, & Aim G. (1997) *Biotherapy;* 10:1-5; Tefferi A, & Grendahl D. C. (1996) *Am. J. Hematol.;* 52: 231-233; Milella M, et al (1995) *Hepatogastroenterology;* 42:201-204].

The reason for the development of antibodies to recombinant IFNα is unclear since the protein is present naturally and expression increases sporadically in response to events such as viral infection. The route and frequency of dosing, the immune modulatory effects of IFNα, and the presence of protein aggregates in the pharmaceutical preparations may all play a role in the breakdown of immune tolerance. However, irrespective of any facilitating factors, the pivotal feature leading to the induction of an immune response is the presence within the protein of peptides that can stimulate the activity of T-cells via presentation on MHC class II molecules. Such peptide sequences are "T-cell epitopes" and are commonly defined as any amino acid residue sequence with the ability to bind to MHC Class II molecules. Implicitly, a "T-cell epitope" means an epitope which when bound to MHC molecules can be recognised by a T-cell receptor (TCR), and which can, at least in principle, cause the activation of these T-cells by engaging a TCR to promote a T-cell response.

From the foregoing there is clearly a continued need for INFα2 analogues with enhanced properties. Desired enhancements include alternative schemes and modalities for the expression and purification of the therapeutic, but also and especially, improvements in the biological properties of the protein. There is a particular need for enhancement of the in vivo characteristics when administered to the human subject. In this regard, it is highly desired to provide INFα2 with reduced or absent potential to induce an immune response and enhanced biological potency in the human subject.

The inventors have previously disclosed the critical regions of the IFNα2 molecule comprising the T-cell epitopes driving the immune responses to this autologous protein and have provided compositions that reduce the effectiveness or wholly eliminate these sequences from being able to act as T-cell epitopes [WO 02/085941]. Such compositions have been achieved by alteration of the amino acid sequence of the IFNα2 protein, for example by substitution, and the present invention is concerned also with IFNα2 molecules in which amino acid substitution and or combinations of substitution have been conducted. However in the present case, new substitutions and combinations of substitutions made confer the surprising property of significantly enhancing the biological activity of the molecule and such an enhancement in combination with substitutions achieving a reduced immunogenic profile for the protein provide for an improved IFNα2 molecule.

Others have provided modified INFα2 and methods of use and include for example U.S. Pat. No. 4,496,537; U.S. Pat. No. 5,972,331; U.S. Pat. No. 5,480,640; U.S. Pat. No. 5,190,751; U.S. Pat. No. 4,959,210; U.S. Pat. No. 5,609,868; U.S. Pat. No. 5,028,422 and others.

U.S. Pat. No. 5,723,125 describes a fusion protein comprising wild-type human IFNα joined via a peptide linker to a human immunoglobulin Fc fragment. The IFNα domain is oriented N-terminal to the Fc domain in the claimed fusion protein.

U.S. Pat. No. 6,204,022 describes IFNα analogues bearing substitutions from WT especially at positions 19, 20, 22, 24 and 27 and characterised by reduced cytotoxicity in a biological assay.

The general category of "human Fc fusion proteins" and suitable vectors for their production have been described previously [U.S. PAT. NO. 5,541,087; U.S. PAT. NO. 5,726,044 Lo et al (1998), *Protein Engineering* 11:495-500].

SUMMARY OF THE INVENTION

The invention provides human interferon alpha 2 molecules containing amino acid substitutions. The amino acid substitutions confer improved properties to the protein. The improved properties concern the specific biological activity of the protein and also the immunogenic properties of the protein.

The molecules of the invention are fusion proteins comprising a human immunoglobulin constant region moiety linked with a human IFNα mutein.

The molecules of the invention have new and inventive properties. Such molecules may cause benefit for a patient suffering from a disease especially suffering from chronic hepatitis C virus infection The molecules of the invention are characterised by the protein sequences defined herein as SEQ ID Nos 2-22.

The molecules of the invention are further characterised by a relative activity in a signalling assay of between greater than 1.3 and 10 fold. In some embodiments the relative activity in a signalling assay is 2 fold or 3 fold or 5 fold or 7 fold or 10 fold or 17 fold.

The molecules of the invention are further characterised yet still by a relative activity in an anti-viral assay of between 2 and 36 fold. In some embodiments the relative activity in an anti-viral assay is 2 fold or greater, or is 3 fold or greater, or is 4 fold or greater, or is 7 fold or greater or is about 36 fold.

A most preferred molecule of the invention is characterised by the protein sequence SEQ ID No 2 and is further characterised by a relative activity of greater than 9 fold in a signalling assay and about 36 fold in an anti-viral assay and about 1 in an anti-proliferation assay.

A further preferred molecule of the invention is characterised by the protein sequence SEQ ID No 3 and is further characterised by a relative activity of greater than 1.3 fold in a signalling assay and about 7.4 fold in an anti-viral assay and about 1 in an anti-proliferation assay.

The molecules of the invention may be further characterised still by activity in an anti-proliferation assay of between 13 and 16 pg (picogram) interferon-α per ml (millilitre). The most preferred molecules of the invention are characterised yet further still by comprising sequences demonstrated to show reduced immunogenicity in human cells.

In summary the invention is concerned with the following issues:

A modified interferon alpha 2 molecule having the biological activity of human interferon alpha 2 containing one or more amino acid substitutions;

a modified interferon alpha 2 molecule having the biological activity of human interferon alpha 2 and comprising a human immunoglobulin constant region (Fc) domain and containing one or more amino acid substitutions within the interferon alpha 2 domain as specified above or below;

a modified interferon alpha 2 molecule having the biological activity of human interferon alpha 2 and comprising a human Fc domain and containing one or more amino acid substitutions within the interferon alpha domain and being further characterised by demonstrating reduced immunogenicity to humans especially in comparison to interferon alpha molecules not containing the amino acid substitutions of the invention;

a general method for the recovery of IFNα muteins with improved properties involving;
  a) identification of T-cell epitopes;
  b) conducting single amino acid substitutions within T-cell epitope regions and selecting functionally active muteins;
  c) optionally, conducting fine mapping studies of critical residues involved in T-cell activation and testing double, or triple of more substitutions for immunogenicity;
  d) selecting individual muteins with the most favoured function and immunogenicity profile for constitution as multiply substituted muteins and function testing said same new proteins;
  e) testing functionally active multiply substituted mutein sequences for reduced immunogenicity using time course immunogenicity assays;

a modified interferon alpha 2 molecule of structure (SEQ ID NO: 24):

$X^0$-CDLPQTHSLGSRRTLMLLAQMRRX$^1$SLFSCLKD RHDFGFPQEEFGNQFQKAETWVLX$^2$EMX$^3$QQIX$^4$N LFSTKDSSAAX$^5$DETLLDKFYTELX$^6$QQLNDLEACVI QGVGVTETPLMKEDSX$^7$LAVRKYFQRITX$^8$YLKEKK YSPCAWEVVRAEIMRS FSLSTX$^9$LQESLRSKE, whereby
$X^0$=Fc or Fc-Linker,
Fc =an Fc domain of an antibody;
Linker =a linker peptide consisting of 6 to 25 amino acids;
$X^1$=I, Q;
$X^2$=H, Y;
$X^3$=I, T;
$X^4$=F, T, A;
$X^5$=W, H;

$X^6$=Y, D;
$X^7$=I, N, T, P, R;
$X^8$=L, T, H, D, S, N; and
$X^9$=N, S;

with the provision that an IFNα molecule wherein simultaneously $X^1$=I, $X^2$=H, $X^3$=I, $X^4$=F, $X^5$=W, $X^6$=Y, $X^7$=I, $X^8$=L and $X^9$=N is excluded. In other words: the provision excludes the wild-type IFN fusion proteins.

In particular the invention relates to

An IFNα2 mutein, wherein
  $X^5$=H and $X^8$=N.
An IFNα2 mutein, wherein
  $X^3$=T and $X^4$=A.
An IFNα2 mutein, selecting from the group consisting of the following compounds:
  (i) $X^1$=Q, $X^2$=H, $X^3$=T, $X^4$=A, $X^5$=H, $X^6$=Y, $X^7$=R, $X^8$=N and $X^9$=N
  (ii) $X^1$=Q, $X^2$=H, $X^3$=I, $X^4$=F, $X^5$=H, $X^6$=Y, $X^7$=I, $X^8$=L and $X^9$=N
  (iii) $X^1$=I, $X^2$=H, $X^3$=T $X^4$=A, $X^5$=H, $X^6$=Y, $X^7$=T, R or N, $X^8$=N and $X^9$=N
  (iv) $X^1$=I, $X^2$=H, $X^3$=T, $X^4$=A, $X^5$=H, $X^6$=Y, $X^7$=I, $X^8$=L and $X^9$=N
  (v) $X^1$=I, $X^2$=Y, $X^3$=I, $X^4$=T, $X^5$=H, $X^6$=Y, $X^7$=I, $X^8$=L and $X^9$=N
  (vi) $X^1$=I, $X^2$=H, $X^3$=I, $X^4$=F, $X^5$=H, $X^6$=Y, $X^7$=P,T or N, $X^8$=L and $X^9$=N
  (vii) $X^1$=I, $X^2$=H, $X^3$=I, $X^4$=F, $X^5$=H, $X^6$=Y, $X^7$=I, $X^8$=T and $X^9$=S
  (viii) $X^1$=I, $X^2$=H, $X^3$=T, $X^4$=F, $X^5$=H, $X^6$=Y, $X^7$=I, $X^8$=T and $X^9$=S
  (ix) $X^1$=I, $X^2$=H, $X^3$=T, $X^4$=F, $X^5$=W, $X^6$=Y, $X^7$=I, $X^8$=T and $X^9$=S
  (x) $X^1$=I, $X^2$=H, $X^3$=I, $X^4$=F, $X^5$=W, $X^6$=Y, $X^7$=I, $X^8$=T, S, N, H or D and $X^9$=N
  (xi) $X^1$=I, $X^2$=H, $X^3$=I, $X^4$=F, $X^5$=H, $X^6$=Y, $X^7$=I, $X^8$=L and $X^9$=N
  (xii) $X^1$=I, $X^2$=H, $X^3$=I, $X^4$=F, $X^5$=W, $X^6$=D, $X^7$=I, $X^8$=L and $X^9$=N An IFNα2 mutein, wherein Fc is a human immunoglobulin heavy chain constant region domain, which is linked by its C-terminus to said mutein.
An IFNα2 mutein, wherein the Fc domain is a monomer.
An IFNα2 mutein, wherein the linker peptide consists of 12 to 20 amino acids.
An IFNα2 mutein, wherein the linker peptide is $(G)_4S(G)_4S(G)_4SG$ (SEQ ID NO: 28).

For the avoidance of doubt, the particularly advantageous muteins of IFNα2 and which are each embodiments of the invention are characterised according to the details of FIG. 1.

The mutant proteins of the present invention are readily made using recombinant DNA techniques well known in the art and the invention provides methods for the recombinant production of such molecules.

In as far as this invention relates to modified INFα2, compositions containing such modified INFα2 proteins or fragments of modified INFα2 proteins and related compositions should be considered within the scope of the invention. In another aspect, the present invention relates to nucleic acids encoding modified INFα2 entities. In a further aspect the present invention relates to methods for therapeutic treatment of humans using the modified INFα2 proteins.

DETAILED DESCRIPTION OF THE INVENTION

In nature, the mature INFα2 protein is single polypeptide of 165 amino acids Several different subtypes of human INFα2 are known, each showing minor differences between primary amino acid sequences. Thus INFα2a and INFα2b differ in only one residue at position 23 of the mature protein chain being lysine in INFα2a and arginine in INFα2b. Whilst the disclosures of the present invention are directed towards the sequence of INFα2b, it can be seen that for all practical purposes the sequence of INFα2a may be considered interchangeably with the subject INFα2b subtype of the present invention. The amino acid sequence of INFα2b (SEQ ID NO: 25; depicted as single-letter code) is as follows:

CDLPQTHSLGSRRTLMLLAQMRRISLFS-CLKDRHDFGFPQEEFGNQFQKAETIPVL-HEMIQQIFNL FSTKDSSAAWDETLLDK-FYTELJYQQLNDLEACVIQGVGVTETPLMKEDSILAV RKYFQRITLYLKE KKYSPCAWEVVRAEIMRSFSLST-NLQESLRSKE.

The term "IFNα" is used herein to denote human interferon alpha 2. In some instances the term is also used more broadly herein to include fusion proteins (see below) comprising an interferon alpha moiety and or more especially an interferon alpha mutein.

The term "mutein" is used herein to denote an IFNα protein engineered to contain one or more amino acid substitutions differing from the above native sequence.

The term "peptide" as used herein, is a compound that includes two or more amino acids. The amino acids are linked together by a peptide bond.

A peptide bond is the sole covalent linkage between amino acids in the linear backbone structure of all peptides, polypeptides or proteins. The peptide bond is a covalent bond, planar in structure and chemically constitutes a substituted amide. An "amide" is any of a group of organic compounds containing the grouping —CONH—.

There are 20 different naturally occurring amino acids involved in the biological production of peptides, and any number of them may be linked in any order to form a peptide chain or ring. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Some peptides contain only a few amino acid units. Short peptides, e.g., having less than ten amino acid units, are sometimes referred to as "oligopeptides". Other peptides contain a large number of amino acid residues, e.g. up to 100 or more, and are referred to as "polypeptides". By convention, a "polypeptide" may be considered as any peptide chain containing three or more amino acids, whereas a "oligopeptide" is usually considered as a particular type of "short" polypeptide. Thus, as used herein, it is understood that any reference to a "polypeptide" also includes an oligopeptide. Further, any reference to a "peptide" includes polypeptides, oligopeptides, and proteins. Each different arrangement of amino acids forms different polypeptides or proteins. The number of polypeptides—and hence the number of different proteins—that can be formed is practically unlimited.

Since the peptide bond is the sole linkage between amino acids, all peptides, polypeptides or proteins have defined termini conventionally referred to as the "N-terminus" or "N-terminal" residue and the "C-terminus" or "C-terminal residue". The N-terminal residue bears a free amino group, whereas the C-terminal residue bears a free carboxyl group.

All sequences of consecutive amino acids accordingly have an orientation N-terminal to C-terminal. Where fusion proteins are constituted or differing domains are connected within a protein species their relative orientation may be described as "N-terminal" or "C-terminal".

The term "fusion protein" is used herein to refer to a protein molecule comprising two or more functionally distinct protein domains within a single polypeptide chain. The protein moieties in the fusion protein may be directly coupled or may be joined via a linker peptide.

A "linker" or "linker peptide" refers herein to a peptide segment joining two moieties of fusion protein. Linker peptides suitable for this invention include peptide having 5 to 25 amino acids, preferably 10 to 20 amino acids, more preferably 15-20 amino acids. An example of a linker peptide is provided by the generic formula $((G)_4S)_xG$, wherein x is 1, 2, 3 or 4 (SEQ ID NO: 26, 27, 28, and 29, respectively). The linker peptide preferred according to the present invention is $(G)_4S(G)_4S(G)_4SG$ (SEQ ID NO: 28). However also other linker peptides of the prior art which have more than 10 amino acids are preferably suitable. U.S. Pat. No. 5,723,125 claims a hybrid interferon molecule of type IFN-L-Fc (where L=linker) wherein the linker sequence is GGSGGSGGGGSGGGGS (SEQ ID NO: 30). The said linker is 16 residues and is considered "comparatively long". The above linker is a variant of the well known peptide linker $(GGGGS)_3$ (SEQ ID NO: 31) described by Huston et al (1988) *Proc Natl. Acad. Sci. USA* 85:5879. Further shorter sequence variants of this linker are also known, such as $(GGGGS)_n$ wherein n=1, 2 or 3 (SEQ ID NO: 32, 33, and 31, respectively) to give a linker of 5, 10 or 15 residues described in Holliger. et al (1993) *Proc Natl. Acad. Sci. USA* 90:6444. A particularly short version of this linker comprising 4 residues (GGGG: SEQ ID NO: 34) has been used in U.S. Pat. No. 6,686,179. Other examples of peptide linkers recognised in the art include all of the following: $(A)_3$, $(A)_4$ (SEQ ID NO: 35), $(A)_5$ (SEQ ID NO: 36), GG, GS, GGG, $(G)_7$ (SEQ ID NO: 37), GPG, GGPGG (SEQ ID NO: 38), and EFGGGGGTA (SEQ ID NO: 39).

Fusion proteins are commonly produced by means of recombinant DNA techniques and as such can be considered artificial proteins having no direct counterparts in nature (natural fusion proteins can arise, for example via chromosomal translocation, but are not considered here). An example of a fusion protein is a fusion in which an immunoglobulin Fc region is placed at the N-terminus of another protein such as IFNα. Such a fusion is termed an "Fc-X" fusion, where X is a ligand (such as IFNα) and Fc-X proteins have a number of distinctive, advantageous biological properties. In particular, whereas such fusion proteins can still bind the relevant Fc receptors on cell surfaces, when the ligand binds to its receptor, the orientation of the Fc region is altered such that antibody-dependent cell-mediated cytotoxicity and complement fixation are activated by the sequences present in the Fc domain. Fc-X fusions are preferred according to the invention.

The term "immunoglobulin" is used herein to refer to a protein consisting of one or more polypeptides substantially encoded by immunoglobulin genes. The recognised immunoglobulin genes include the κ, λ, α, γ (IgG1, IgG2, IgG3, IgG4), σ, ε, and μ constant region genes and in nature multiple immunoglobulin variable region genes.

The term Fc is used herein to refer to an immunoglobulin heavy chain constant region domain and includes the dimeric as well as the monomeric form of the Fc portion of an antibody. Preferably the single chain Fc fusion (monmeric) form is preferred.

The term "T-cell epitope" means according to the understanding of this invention an amino acid sequence which is able to bind MHC class II, able to stimulate T-cells and/or also to bind (without necessarily measurably activating) T-cells in complex with MHC class II.

Reference to "substantially non-immunogenic" or "reduced immunogenic potential" includes reduced immunogenicity compared to a parent protein or to a fusion protein containing the wild-type or native amino acid sequences of the test moiety.

The term "immunogenicity" includes an ability to provoke, induce or otherwise facilitate a humoral and or T-cell mediated response in a host animal and in particular where the "host animal" is a human.

The terms "T-cell assay" and "immunogenicity assay" concern ex vivo measures of immune reactivity. As such these involve a test immunogen e.g. a protein or peptide being brought into contact with live human immune cells and their reactivity measured. A typical parameter of induced reactivity is proliferation. The presence of suitable control determinations are critical and implicit in the assay.

"Time course assay" refers to a biological assay such as a proliferation assay in which determinations of activity are made sequentially over a period of time. In the present context, a "time course T-cell assay", refers to the determination of T-cell proliferation in response to a test immunogen (peptide) at multiple times following exposure to the test immunogen. The terms "time course T-cell assay" and "time course immunogenicity assay" may be used interchangeably herein.

One conventional way in which T-cell assays are expressed is by use of a "stimulation index" or "SI". The stimulation index (SI) is conventionally derived by division of the proliferation score (e.g. counts per minute of radioactivity if using for example.$^3$H-thymidine incorporation) measured to a test immunogen such as a peptide by the score measured in cells not contacted with a test immunogen. Test immunogens (peptides) which evoke no response give SI=1.0 although in practice SI values in the range 0.8-1.2 are unremarkable. The inventors have established that in the operation of such immunogenicity assays, a stimulation index equal to or greater than 2.0 is a useful measure of significant induced proliferation.

PBMC means peripheral blood mononuclear cells in particular as obtained from a sample of blood from a donor. PBMC are readily isolated from whole blood samples using a density gradient centrifugation technique well understood in the art and comprise predominantly lymphocytes (B and T cells) and monocytes. Other cell types are also represented.

"Relative activity" means according the present context activity measured for a test protein in any single assay expressed relative to the activity measured for a positive control protein in an identical assay and usually conducted in parallel. Thus if the test protein and the control protein have the same measured activity the relative activity is said to be 1.

An anti-viral assay is a biological assay in which a test protein of interest is measured for any ability to inhibit functioning of a viral agent on suitable host cells. Such an assay is generally configured such that anti-viral activity is becomes equated with prolonged cellular survival or proliferation in the presence of cytopathic doses of virus. For this to be a useful measure suitable control tests are conducted in parallel. The presence of suitable control determinations are critical and implicit in the assay. One particularly suitable antiviral assay is described by Rubinstein et al [Rubinstein S, et al (1981) *J Virol.* 37:755-758] and is exemplified herein. Other assay formats can be contemplated and also provide quantitative estimations of specific activity of the test molecules to permit $ED_{50}$ determinations.

A "signalling assay" according to the present context means a biological assay able to provide a reading of the ability of a test protein to evoke a specific measurable response inside a live cell. In particular the test protein is brought into contact with the outside surface of the cell and the measured response is a phenomenon that can occur only with the involvement of a least one specific receptor protein and multiple cellular factors within the cell such as transcription factors. Collectively the receptor and the other multiple cellular factors constitute a "signalling pathway" and such a pathway is known to be activated by functionally active IFN proteins [Williams, B. R. (1991) *Eur. J. Biochem.* 15: 1-11; David, M. (1995) *Pharmacol. Ther.* 65: 149-161]. A particularly suitable signalling assay is exemplified herein, other assay formats can be contemplated to also provide quantitative estimations of specific activity of the test molecules.

An "anti-proliferation" assay is a biological assay in which a test protein of interest is measured for any ability to inhibit the growth of an indicator cell culture. For this to be a useful measure suitable control tests are conducted in parallel. One particularly suitable anti-proliferation assay is described by Mark et al [Mark, D. F. (1984) *Proc. Natl. Acad. Sci. USA* 81: 5662-5666] and in modified form is exemplified herein. Other assay formats can be contemplated and also provide quantitative estimations of specific activity of the test molecules to permit $ED_{50}$ determinations.

In another aspect, the present invention relates to nucleic acids encoding modified IFNα entities. Such nucleic acids are preferably comprised within an expression vector. The control sequences that are suitable for prokaryotes, for example, include a promoter, optionally an operator sequence, and a ribosome binding site. Eukaryotic cells are known to utilise promoters, enhancers and polyadenylation signals. Such nucleic acids in general comprise a selection means typically an additional gene encoding a protein able to provide for the survival of the host cell. An example of such a selection gene is the beta-lactamase gene suitable for some *E.coli* host cells and this and others are well known in the art ["Molecular Cloning: A Laboratory Manual", second edition (Sambrook et al., 1989); "Gene Transfer Vectors for Mammalian Cells" (J. M. Miller & M. P. Calos, eds., 1987); "Current Protocols in Molecular Biology" (F. M. Ausubel et al., eds., 1987)].

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in the same reading frame. However, enhancers do not have to be contiguous. Linking is accomplished by ligation at convenient restriction sites. If such sites do not exist, the synthetic oligonucleotide adaptors or linkers are used in accordance with conventional practice.

In some embodiments the expression vector comprises a nucleic acid sequence encoding an IFNα variant operably linked to an expression control sequence. In various embodiments the expression vector comprises a nucleic acid sequence encoding a protein selected from the group comprising inclusively SEQ ID No 2 to SEQ ID No 22. Such an expression vector will comprise at least the IFNα encoding domain of one of the said proteins operably linked with suitable expression control and selection sequences. Such an expression vector would include degenerate versions of the nucleic acid wherein degeneracy in relation to polynucleotides refers to the fact well recognised that in the genetic code many amino acids are specified by more than one codon. The degeneracy of the code accounts for 20 different amino acids encoded by 64 possible triplet sequences of the four different bases comprising DNA.

Another aspect of the present invention is a cultured cell comprising at least one of the above-mentioned vectors.

A further aspect of the present invention is a method for preparing the modified IFNα comprising culturing the above mentioned cell under conditions permitting expression of the IFNα from the expression vector and purifying the IFNα from the cell.

In a further aspect, the present invention relates to methods for therapeutic treatment of humans using the IFNα compositions. For administration to an individual, any of the modified compositions would be produced to be preferably at least 80% pure and free of pyrogens and other contaminants. It is further understood that the therapeutic compositions of the IFNα proteins may be used in conjunction with a pharmaceutically acceptable excipient. The pharmaceutical compositions according to the present invention are prepared conventionally, comprising substances that are customarily used in pharmaceuticals, e.g. Remington's Pharmaceutical Sciences, (Alfonso R. Gennaro ed. 18$^{th}$ edition 1990), including excipients, carriers adjuvants and buffers. The compositions can be administered, e.g. parenterally, enterally, intramuscularly, subcutaneously, intravenously or other routes useful to achieve an effect. Conventional excipients include pharmaceutically acceptable organic or inorganic carrier substances suitable for parenteral, enteral and other routes of administration that do not deleteriously react with the agents. For parenteral application, particularly suitable are injectable sterile solutions, preferably oil or aqueous solutions, as well as suspensions, emulsions or implants, including suppositories. Ampules are convenient unit dosages. The pharmaceutical preparations can be sterilised and, if desired, mixed with stabilisers, wetting agents, emulsifiers, salts for influencing osmotic pressure, buffers or other substances that do not react deleteriously with the active compounds.

The major embodiments of the present invention are encompassed by the protein sequences SEQ ID NO: 2-22. The proteins are fusion proteins of the type "Fc-X" wherein X in this present instance comprise IFNα muteins. Such fusion proteins have been found to show increased activity compared to the fusion proteins containing the wild-type (WT) IFNα moiety. The "WT" or "native" fusion proteins constructed by the inventors herein have been designated IFN120 (SEQ ID NO: 23) and IFN5 (SEQ ID NO: 1) and differ only with respect to the presence or absence of a linker peptide of structure $(G)_4S(G)_4S(G)_4SG$ (SEQ ID NO: 28). For clarity, IFN5 does not contain the linker.

Using a signalling assay, the native fusion proteins, either with or without the linker, have been found herein to have very similar $ED_{50}$ values of 4.5 and 5 ng/ml. This finding demonstrates that for native IFNα, the presence of a linker between the Fc and IFNα molecules has no effect on activity.

By contrast, it has been somewhat surprisingly found that the most preferred molecules of the invention IFN311 (SEQ ID No 3) and IFN316 (SEQ ID No 2) have $ED_{50}$ values of 3.4 and 0.5 ng/ml in a signalling assay and are hence >1.3× and >9× more active than controls. Given that these molecules are INFα muteins, these results indicate that the changes to the sequence have had a beneficial effect on activity.

Other IFNα muteins containing two or three or four or five amino acid substitutions were also found with improved relative activity with respect to the signalling assay. Examples each with two substitutions include IFNα proteins IFN197 (SEQ ID No 12), IFN201 (SEQ ID No 11), IFN202 (SEQ ID No 10), IFN306 (SEQ ID No 4) demonstrating respectively 2, 7, 5 and 4 fold improvement in activity. Also proteins IFN173 (SEQ ID No 15), IFN176 (SEQ ID No 13), IFN219 (SEQ ID No 9) each with three substitutions demonstrating respectively 10, 5, and 17 fold improvement in activity. INFα protein IFN174 (SEQ ID No 14) with four substitutions showed a 5 fold improvement in signalling activity.

Such beneficial effects with respect to activity in a signalling assay are not confined to muteins containing multiple substitutions. Thus for example single mutant IFNα protein IFN28 (SEQ ID No 22) exhibits a 10 fold increased relative activity. Similarly, protein IFN64 (SEQ ID No 21) shows greater than 3 fold increased activity, IFN164 (SEQ ID No 20) shows 3 fold increased activity, proteins IFN167 (SEQ ID No 19) and IFN168 (SEQ ID No 18) both show 2 fold improvement, protein IFN171 (SEQ ID No 17) shows a 4 fold improvement and protein IFN172 (SEQ ID No 16) shows a 7 fold improvement with respect to signalling activity.

Whilst signalling activity is a useful indicator of IFNα protein functionality and has been used by the inventors as a rapid screening assay for IFNα muteins, anti-viral activity is the recognised international standard for measuring the potency of IFNα and to a degree a more realistic surrogate of possible clinical activity. Anti-viral activity can therefore be used to compare the activity of the different IFNα molecules and the inventors have used such in the present case to confirm that the most preferred molecules of the invention show activity within the range of clinically validated IFNα preparations. More specifically, fusion protein IFN316 has 13% standard activity, whereas Peg-Intron®, Pegasys® and Albuferon® have been reported to have 28%, 10% and 7% respectively [Osborn B L, et al. (2002);*J Pharmacol Exp Ther.* 303:540-548; Grace M, et al (2001) *J Interferon Cytokine Res.* 21:1103-1115; Bailon P, et al (2001) *Bioconjug Chem.* 12:195-2029,10,11]

The anti-viral activity of the protein is a function of the ability of the protein to evoke the intracellular signalling pathway as extends from the interferon receptor to new gene expression in the nucleus of the cell. Concordance between improvements in signalling activity and anti-viral activity is an expected result and has been shown to be the case for the IFNα muteins of the invention. Thus the IFNα proteins, IFN270 (SEQ ID No 7), IFN273 (SEQ ID No 6) and IFN276 (SEQ ID No 5) each with five substitutions demonstrated respectively a 2 fold, a 3 fold and a further 3 fold improvement in relative signalling activity whilst also demonstrating a greater than 6 fold, a greater than 4 fold and a further greater than 4 fold improvement respectively in relative anti-viral activity. One IFNα mutein showed no improvement in signalling activity being equal to the control in this aspect but yet showed greater than 2 fold (about 2.8) improvement in anti-viral activity. This mutein was protein IFN248 (SEQ ID No 8) and contained 3 substitutions.

The IFNα muteins of the present were constructed to be less immunogenic than the parental molecule. The design of individual muteins was directed from immunological considerations as well as functional activity data. The three regions of immunological importance within the molecule was defined using screening assays involving PBMC preparations from both healthy donor subjects and individuals who had previously received therapeutic IFNα IntronA®). Broadly, IFNα muteins were constructed containing mutations within the three identified immunogenic regions. Residues were targeted based upon the known binding properties of HLA-DR molecules in that they have an almost exclusive preference for a hydrophobic amino acid in pocket 1 and that this is the most important determinant of peptide binding [Jardetzky, T. S. et al (1990), *EMBO J.* 9: 1797-1803; Hill, C. M. et al (1994) *J. Immunol.* 152: 2890-2898]. Exhaustive mutational analysis identified those residues within these regions that could be altered without adversely affecting the activity of the fusion protein (Table 2). Choice of alternate residue was guided by the location of the target in the solved NMR structure [Klaus, W. et al (1997), *J. Mol. Biol.* 274: 661-675] and comparison to other human IFNα proteins and those from other species. Buried residues were replaced with either alanine or similar sized non-hydrophobic residues whereas exposed residues were scanned with all possible non-hydrophobic alternatives.

T-cell assays were also applied in a format to enable fine mapping of the critical residues involved in functional activation of the human T-cells. These studies were done using a family of variant synthetic peptides to scan the region of interest and using known responsive donor samples. Mutation scanning T-cell assays were performed using alanine as the scanning amino acid, except where activity data was already available to guide the choice. Such an approach is able to highlight the contribution of individual amino acid residues to the immunogenicity of the T-cell epitope comprising its locale. Whilst it would be most desired to alter a critical residue involved in the immunogenicity this may not always be compatible with retaining protein function. Multiple substitutions can be employed none of which in isolation are able to eliminate immunogenicity, but which none the less in combination are effective in reducing the immunogenic potential of an otherwise immunogenic region. In the present case, epitope fine mapping studies (Table 4) followed by T-cell assays of combinatorial mutants (Table 5) was able to define combinations of substitutions best able to both retain function and demonstrate reduced immunogenicity in the region of interest.

Further corroborative T-cell assays were conducted using synthetic peptides containing whole combinations of multiple mutation sets (Table 3) to demonstrate reduced immunogenicity in the most desired substitution sets. These latter assays were conducted using synthetic peptides spanning each of the 3 immunogenic regions of the molecule and were run as time-course T-cell assays using PBMCs from both healthy donors and patients who had previously been treated with IntronA®. It will be recognised that it is not possible to test purified proteins in T-cell assays due to their anti-proliferative properties.

A general method for the recovery of IFNα muteins with improved properties involves therefore;

a) identification of T-cell epitopes;

b) conducting single amino acid substitutions within T-cell epitope regions and selecting functionally active muteins;

c) optionally, conducting fine mapping studies of critical residues involved in T-cell activation and (optionally) testing double, or triple of more substitutions for immunogenicity;

d) selecting individual muteins with the most favoured function and immunogenicity profile for constitution as multiply substituted muteins and function testing said same new proteins;

e) testing functionally active multiply substituted mutein sequences for reduced immunogenicity using time course immunogenicity assays.

Taken together, the inventors have been able to define improved IFNα proteins which can be depicted by the following structure (SEQ ID NO: 24):

The following, figures, sequence listing and examples are provided to aid the understanding of the present invention. It is understood that modifications can be made in the procedures set fourth without departing from the spirit of the invention.

DESCRIPTION OF THE SEQUENCES

To aid the understanding of the invention, Table 1 below sets out a description of the fusion protein IFNα muteins. The derivation and properties of these proteins are also more fully disclosed in the examples.

TABLE 1

Description of the sequences

| Clone ID | Substitution(s)* | SEQ ID No |
|---|---|---|
| IFN5 | None = WT | SEQ ID No 1 |
| IFN316 | I24Q, I60T, F64A, W76H, I116R, L128N | SEQ ID No 2 |
| IFN311 | I24Q, I60T, F64A, W76H, I116R, L128N | SEQ ID No 3 |
| IFN306 | I24Q, W76H | SEQ ID No 4 |
| IFN276 | I60T, F64A, W76H, I116T, L128N | SEQ ID No 5 |
| IFN273 | I60T, F64A, W76H, I116R, L128N | SEQ ID No 6 |
| IFN270 | I60T, F64A, W76H, I116N, L128N | SEQ ID No 7 |
| IFN248 | I60T, F64A, W76H | SEQ ID No 8 |
| IFN219 | H57Y, F64T, W76H | SEQ ID No 9 |
| IFN202 | W76H, I116P | SEQ ID No 10 |
| IFN201 | W76H, I116T | SEQ ID No 11 |
| IFN197 | W76H, I116N | SEQ ID No 12 |
| IFN176 | W76H, L128T, N156S | SEQ ID No 13 |
| IFN174 | I60T, W76H, L128T, N156S | SEQ ID No 14 |
| IFN173 | I60T, L128T, N156S | SEQ ID No 15 |
| IFN172 | L128T | SEQ ID No 16 |
| IFN171 | L128S | SEQ ID No 17 |
| IFN168 | L128N | SEQ ID No 18 |
| IFN167 | L128H | SEQ ID No 19 |
| IFN164 | L128D | SEQ ID No 20 |
| IFN64 | W76H | SEQ ID No 21 |
| IFN28 | Y89D | SEQ ID No 22 |
| IFN120 | None = WT | SEQ ID No 23 |

*The residue numbering for the IFN substitutions commences from residue 1 of the IFN reading frame and is independent of any Fc component.

DESCRIPTION OF THE FIGURES

FIG. 1 sets out the relative biological activities of each of the preferred IFNα muteins of the invention. The clone ID numbers and the substitutions conducted within each clone are as indicated. The figures denote the relative activities determined for IFN receptor mediated cell activation (=signalling assay), anti-viral activity and anti-proliferation activity using the biological assays set out in Examples. All activities are depicted relative to the Fc-IFNa protein IFN5, which has the WT INFα moiety in direct fusion to an N-terminal Fc domain.

FIG. 3 shows comparisons of the activity of purified IFN311 and IFN316 to Peprotech IFNα2a.

Figure 2:
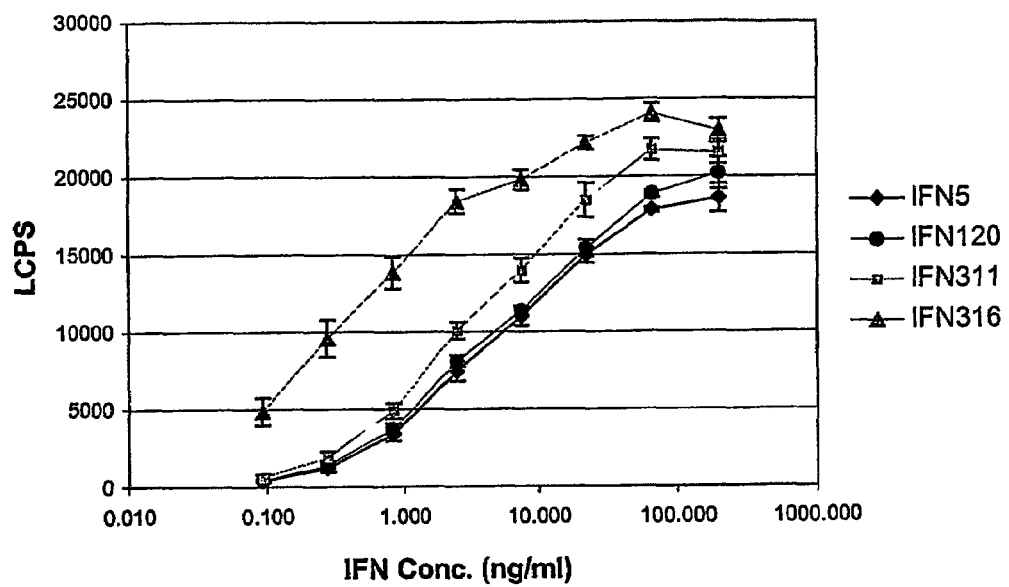
FIG. 2 shows results of receptor signalling assay of cell-culture supernatants. HEK293 cells were transiently transfected with plasmids coding for IFN5, IFN120, IFN316 and IFN311. Protein concentration in the supernatants were quantified by Fc ELISA and diluted to 200 ng/ml. The activity was titrated in 3 fold serial dilutions.

(a) Receptor signalling assay. Titrations were started from 200 ng/ml followed by 3 fold serial dilutions.

(b) Daudi cell anti-proliferation assay. Titrations were started from 200 ng/ml followed by 4 fold serial dilutions.

(c) Anti-viral assay. Initial concentrations were 250 pg/ml for IFN311, 62.5 pg/ml for IFN316 and 6.25 pg/ml for IFNα2a and titrations were done in 2 fold serial dilutions. Each graph shows data averaged from three experiments.

FIG. 4 shows results of time course immunogenicity assays using synthetic peptides (NB: peptide sequences are given in Table 3). 20 healthy individuals and 20 HCV patients (treated with IntronA®) were used to assess the immunogenicity of wild type and modified IFNα peptides. Proliferation of PBMCs was assessed by tritiated thymidine incorporation on days 6, 7, 8 and 9 post-stimulation.

(a) Positive responses (SI>2) from healthy individuals after stimulation with peptides spanning Regions 1, 2 and 3.

(b) Positive responses (SI>2) from HCV patients after stimulation with peptides spanning Regions 1, 2 and 3.

(c) Frequency of observed responses with an SI>2 at any time point from a pool of 20 healthy donors and 20 HCV patients to peptides spanning immunogenic Regions 1, 2 and 3.

FIGS. 5.1-5.12 show protein sequences of the preferred molecules of the invention, i.e., SEQ ID NO: 2-22, as well as comparative fusion proteins having SEQ ID NO: 1 and SEQ ID NO: 23. In FIG. 5.1, IFN 5 is SEQ ID NO: 1 and IFN 28 is SEQ ID NO: 22. In FIG. 5.2, IFN64 is SEQ ID NO: 21 and IFN164 is SEQ ID NO: 20. In FIG. 5.3, IFN167 is SEQ ID NO: 19 and IFN168 is SEQ ID NO: 18. In FIG. 5.4, IFN171 is SEQ ID NO: 17 and IFN172 is SEQ ID NO: 16. In FIG. 5.5, IFN173 is SEQ ID NO: 15 and IFN174 is SEQ ID NO: 14. In FIG. 5.6, IFN176 is SEQ ID NO: 13 and IFN197 is SEQ ID NO: 12. In FIG. 5.7, IFN201 is SEQ ID NO: 11 and IFN202 is SEQ ID NO: 10. In FIG. 5.8, IFN219 is SEQ ID NO: 9 and IFN248 is SEQ ID NO: 8. In FIG. 5.9, IFN270 is SEQ ID NO: 7 and IFN273 is SEQ ID NO: 6. In FIG. 5.10, IFN276 is SEQ ID NO: 5 and IFN306 is SEQ ID NO: 4. In FIG. 5.11, IFN311 is SEQ ID NO: 3 and IFN316 is SEQ ID NO: 2. In FIG. 5.12, IFN120 is SEQ ID NO: 23. Sequences are depicted in single letter code. The Fc and Fc-linker moiety of each fusion protein is underlined. The IFNα domain is non underlined. The clone ID numbers are shown for each sequence.

EXPERIMENTAL EXAMPLES

Example 1

Cloning and Mutagenesis of IFNα2b

The modified IFNα proteins of the present invention were made using conventional recombinant DNA techniques. The coding sequence for mature IFNα2b was cloned from human placental DNA (Sigma, Poole, UK) using PCR. The wild-type gene was used both as a control reagent and a template from which to derive modified IFN proteins by site directed mutagenesis. WT and modified genes were inserted into an expression vector pdC-huFc [Lo K-M et al, (1998) *Protein Eng* 11:495-500] such that the IFNα2b sequence is a direct fusion to the C-terminus of the hinge/CH2/CH3 Fc region of human IgG1. The WT IFN protein in this vector was designated IFN5.

In addition to the direct fusion, a modification of the vector was made which contained a flexible linker between the C-terminus of the CH3 and the N-terminus of IFNα2b. The amino-acid sequence of this linker was (G)$_4$S(G)$_4$S(G)$_3$SG (SEQ ID NO: 40) and the WT IFN protein with the linker was designated IFN 120. Some of the mutant IFN proteins were expressed in both vector types thus for example variants IFN311 (SEQ ID NO: 3) and IFN316 (SEQ ID NO: 2) whilst comprising identical substitution sets within their IFN domains differ in respect of the (G)$_4$S(G)$_4$S(G)$_3$SG (SEQ ID NO: 40) linker. IFN311 is a direct fusion, whereas IFN316 contains the linker.

DNA sequencing was conducted on all constructs. This was diligently performed to confirm introduction of desired substitutions and establish that no extraneous (undesired) substitutions had been introduced for example by PCR error.

Details of the techniques and cloning strategy for the WT and variant IFN proteins have been detailed elsewhere [WO 02/085941] and are commonly understood in the art.

Example 2

Design of IFNα Muteins

Variants of IFNα2b linked to the Fc portion of human IgG1 were constructed containing mutations within the three immunogenic regions of the protein. Cycles of mutational analysis involving construction and function testing identified those residues within these regions that could be altered without adversely affecting the activity of the Fc-linked protein. The signalling assay as described herein (see Example 5) was the main screening tool in this aspect. Results of the mutational analysis are shown in Table 2.

TABLE 2

IFNα amino acid residues targeted for mutation

| | Region 1 | | | | |
|---|---|---|---|---|---|
| | $I^{24}$ | $L^{26}$ | $F^{27}$ | $L^{30}$ | $F^{36}$ |
| Substitution | P/Q* | H* | S | A | A |
| Relative Activity⁺ | 4 | 0.25 | 0.1 | 0 | 0 |

| | Region 2 | | | | | |
|---|---|---|---|---|---|---|
| | $I^{60}$ | $I^{63}$ | $F^{64}$ | $L^{66}$ | $F^{67}$ | $W^{76}$ |
| Substitution | T | T | A* | T* | A | H |
| Relative Activity⁺ | 1 | 0.5 | 0.8 | 0 | 0 | 5 |

| | Region 3 | | | | | | |
|---|---|---|---|---|---|---|---|
| | $I^{116}$ | $L^{117}$ | $V^{119}$ | $Y^{122}$ | $F^{123}$ | $I^{126}$ | $L^{128}$ |
| Substitution | T* | H* | A | H | H | A/T | T* |
| Relative Activity⁺ | 2 | 0.9 | 0.5 | 0 | 0.1 | 0.1 | 7 |

*indicates that all non-hydrophobic alternatives were tested with most active shown ⁺determined by receptor signalling assay and compared to Fc linked wt IFNα.

Choice of alternate residue was guided by the location of the target in the solved NMR structure [Klaus, W. et al (1997), *J. Mol. Biol.* 274: 661-675] and comparison to other human IFNα proteins and those from other species. Buried residues were replaced with either alanine or similar sized non-hydrophobic residues whereas exposed residues were scanned with all possible non-hydrophobic alternatives.

In Region 1, the only hydrophobic residue that could be replaced successfully, with a significant improvement in activity, was I24. L26, F27 and L30, although well exposed, could not be changed presumably because they form a well-defined hydrophobic patch with inter-molecular functionality.

In Region 2, the only well-exposed residue was F64 which was changed to A with a modest drop in activity. Residues I60 and I63, although mostly buried, were successfully changed to T, a residue of similar size that can add hydrogen bonds to the alpha-helix in which these residues lie. Residue W76, which lies towards one tip of the molecule, although substantially buried, was changed to H with a significant benefit in activity.

In Region 3, the only residues that could be successfully altered were those that were well exposed. Changes to I116 and L128 gave significant-benefits in activity and alteration of L117 resulted in slightly reduced activity.

Data from scanning T-cell assays conducted on immunogenic Region 3 were also included to further refine the design process (see Tables 4 and 5, Example 9). Whereas immunologically the most favoured single substitution would have been F123, this was not compatible with any useful level of signalling activity. By contrast, the combination of substitutions at residues I116 and L128 were confirmed to modulate the T-cell response to this region. Further substitutions at each position were tested to encompass a range of sizes of side chains that had shown good activity. The substitutions were I116 to T, N and R and L128 to N, H and IL Nine mutants were made containing each combination of these residues in conjunction with those mutations in Regions 1 and 2 that gave acceptable activity (I24Q, I60T, F64A, W76H).

A combined mutein containing I116R and L128N together with I24Q, I60T, F64A, and W76H was constructed in a format that either contained or did not contain a flexible linker between the Fc and IFNα fusion partners (IFN316 and IFN311 respectively).

Example 3

Transfection and Purification of Fusion Proteins

Transient transfections were done using HEK293 (ATCC# CRL-1573) cells and Lipofectamine 2000 (Invitrogen, Paisley, UK) as described by the manufacturer. Stable transfectants were made in NS0 cells (ECACC# 85110503) using electroporation as previously described [Baum C, et al (1994) *Biotechniques* 17:1058-106224] and selected in media containing 100 nM methotrexate. All cell-lines were maintained in DMEM plus 10% FBS with antibiotics and antimycotics. Fusion proteins were purified via Prosep-A chromatography followed by size exclusion chromatography (SEC). Briefly, 1 ml Prosep®-A columns (Millipore, Watford, UK) were equilibrated in PBS pH 7.4 before being loaded with 0.2 μM filtered cell-culture supernatants (up to 500 ml) that had been pH adjusted with 1/20 vols. 1M Tris-HCl pH 7.4. The column was washed with 50 ml PBS pH 7.4 and the fusion protein eluted with 0.1M citrate buffer pH 3.0 and 0.9 ml fractions collected. The fractions were immediately neutralized with 0.1 ml 1M Tris-HCl pH 8.0. SEC was done with Superdex 200 (Amersham Pharmacia, Amersham, UK) in a 3.2/30 column equilibrated and run in PBS pH 7.4 containing 0.1% Tween 80. Fractions spanning the major peak were pooled and fusion proteins quantified using molar extinction coefficients at 280 nm calculated using Lasergene™ software (Dnastar, Madison, Wis., USA). The concentrations were confirmed using a BCA protein assay (Pierce, Chester, UK). The IFNα component represents 42% of the molecular weight of the fusion protein, therefore the concentrations were adjusted by this factor.

Example 4

Quantitation of Fusion Proteins in Cell-culture Supernatants

Fusion proteins were quantified by detecting the amount of human IgG1 Fc in an ELISA format as follows: ELISA plates (Dynex Immulon4) were coated with a mouse monoclonal anti-human IgG Fc specific antibody at a dilution of 1/1500 in PBS pH7.4, 100 µl/well, for 2 h at 37° C. The plate was washed ×4 with 100 µl/well PBS/0.05% Tween 20. Human IgG standards (The Binding Site, Birmingham, UK) were diluted to 2 µg/ml in PBS/2% BSA and duplicate two-fold dilutions made vertically down the plate. Test samples were diluted 1/100 and 1/500 in PBS/2% BSA and assayed in duplicate. The plate was incubated for 1 h at room temperature and washed as before. Detection was done using 100 µl/well goat anti-human IgG Fc-specific peroxidase conjugate (The Binding Site, Birmingham, UK) at a dilution of 1/1000 in PBS, the plate washed as before and colour developed using SigmaFast OPD, 100 µl/well (Sigma, Poole, UK). The colour reaction was stopped by the addition of 50 µl 2M sulphuric acid and the absorbance measured at 492 nm in an Anthos HTII plate reader.

Example 5

Assays for Fc-IFNα2b Activity (Signalling Assay)

Plasmids coding for variant and WT IFN fusion proteins were transfected transiently into HEK293 cells and after three days the cell-culture supernatants were quantified for the Fc portion of the fusion. The supernatants were assayed for activity using a signalling assay. Measurement of activity in this assay requires triggering (activation) of the type I interferon receptor expressed on the cell surface. The activated receptor leads to the activation of the Jak/STAT1 signalling pathway within the cell. The pathway culminates in phosphorylation of protein STAT1 enabling it to bind the Interferon Stimulated Response Element (ISRE). The ISRE is a cis-acting DNA segment which is able to promote transcription of genes (e.g. a reporter gene) linked downstream to it.

The ability of the fusion proteins of the invention to induce signalling from the type I interferon receptor was assayed using a commercially supplied signalling reporter vector, pISRE-TA-luc (Clonetech Europe, Brussels, Belgium). The vector contains the firefly luciferase gene under the control of the Interferon Stimulated Response Element (ISRE). The ISRE/luciferase cassette (on a NotI/BamHI fragment) was transferred to the episomal mammalian expression vector pREP4 (Invitrogen, Paisley, UK) in place of the RSV promoter/MCS/SV40 polyA (removed via SaiI digestion), to create pREP-ISRE. This vector was transfected into HEK293 cells and stable transfectants selected with 100 µg/ml hygromycin to create HEK-ISRE cells. Assays for Fc-IFNα2b activity were done by plating HEK-ISRE cells at a density of $4 \times 10^5$ cells/ml into the wells (100 µl/well) of black walled, clear bottomed 96 well luminometer plates (Greiner, Stonehouse, Glouc., UK) and incubating for 24 h under normal conditions in the absence of antibiotics.

Duplicate serial dilutions of standard IFNα2a $2 \times 10^8$ IU/mg (Peprotech, London, UK) and fusion proteins in antibiotic free media were made down the plate and incubated overnight. Luciferase activity was detected by the addition of 100 µl Steady-Glo reagent (Promega, Southampton, UK) prepared as instructed by the supplier, followed by measurement of luminescence using a Wallac Microbeta Trilux luminometer.

FIG. 1 tabulates the relative activities of each IFNα mutein. FIG. 2 shows signalling activity curves for fusion proteins IFN5, IFN120, IFN311 and IFN316. These results show that the variant fusion proteins have increased activity compared to the native fusion proteins (IFN120 and IFN5, with and without the linker respectively). The native fusion proteins, either with or without the linker, have very similar $ED_{50}$ values of 4.5 and 5 ng/ml respectively, demonstrating that, for native IFNα, the presence of a linker between the Fc and IFNα molecules has no effect on activity. IFN311 and IFN316 have $ED_{50}$ values of 3.4 and 0.5 ng/ml and are hence >1.3× and >9× more active than controls, demonstrating that the changes to the sequence have had a beneficial effect on activity. A surprising result in this assay was found in that in contrast to the native IFNα constructs, the presence of a linker between the Fc and IFNα increased the activity of the fusion protein.

Figure 3:
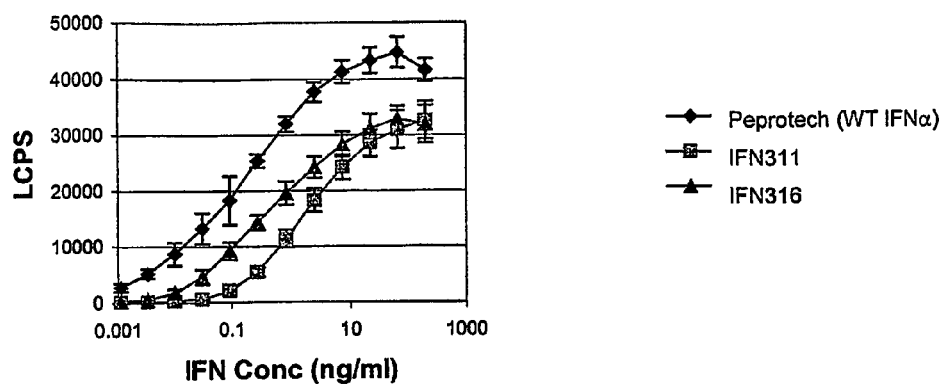
Figure 3:
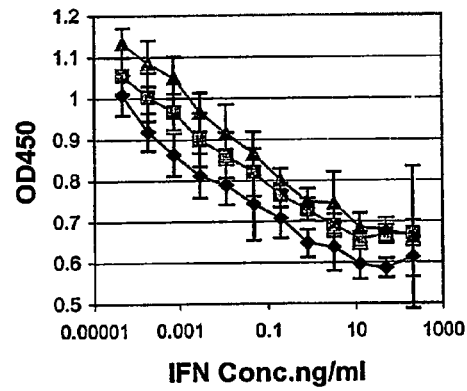
Figure 3:
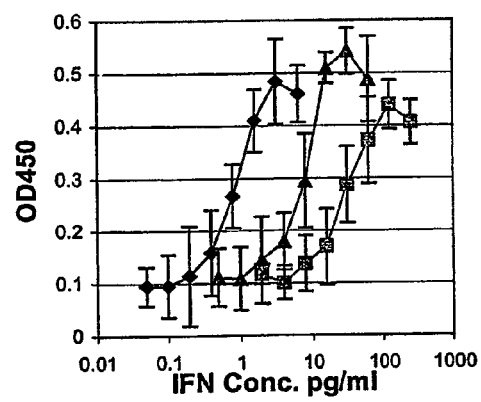

Signalling activity of fusion proteins IFN311 and IFN316 were also compared to a native IFNα preparation (Peprotech, London, UK) and the activity curves are depicted in FIG. 3a.

Example 6

Activities of the Modified Fc-IFNα2b Fusion Proteins (Anti Proliferation)

The anti-proliferative properties of the fusion proteins were assessed by inhibition of Daudi cell proliferation and were performed as follows: Daudi cells (ATCC# CCL-213) were grown in RPMI1640 plus 10% FBS plus antibiotics (Daudi media). Cells in mid log phase were diluted to $2 \times 10^5$ cells/ml and plated out at 75 µl/well into 96 well microtitre plates. Dilutions of standard IFNα2a (Peprotech) and fusion proteins were made in triplicate in 75 µl Daudi media and added to the cells. Serial ¼ dilutions were made across the plate; therefore 1 standard and one test sample were assayed per plate. The plates were incubated for 3 days. Detection was done using Aqueous One reagent (Promega) prepared as described by the manufacturer. 30 µl reagent was added to each well, the plates incubated for 4 h and the absorbance at 492 nm read using an Anthos HTII plate reader.

FIG. 3b shows the anti-proliferative properties plotted for fusion proteins IFN311 and IFN316 relative to a native (non fusion protein) INFα preparation (Peprotech).

Example 7

Activities of the Modified Fc-IFNα2b Fusion Proteins (Anti-viral)

The antiviral properties of the fusion proteins were assayed by the inhibition of cytopathic effect assay of encephalomyocarditis virus (EMCV) on human lung carcinoma A549 cells (ATCC# CCl-185) as previously described [Rubinstein S, et al (1981) *J Virol.* 37: 755-758].

FIG. 1 tabulates the relative activities of several IFNα muteins in this assay. The maximum relative activity was shown by fusion protein IFN316, where the calculated fold increase over the control was 36. The surprising result is that the presence of the linker in IFN316 has a marked beneficial effect on its anti-viral activity compared to the linker free counterpart IFN311 (relative activity=7.4). This marked difference is not seen in comparing the WT IFNα fusion proteins with and without the linker (IFN5 versus IFN120). FIG. 3c shows the anti-viral activity properties plotted for fusion proteins IFN311 and IFN316 relative to a native (non fusion protein) INFα preparation (Peprotech).

Example 8

T-cell Epitope Mapping of Human IFNα and Analysis of Immunogenic Regions by Time-course T-cell Assays The initial T-cell epitope mapping study of human IFNα was conducted using synthetic peptides and PBMC from healthy donors and the results and details of this assay have been described elsewhere [WO 02/085941]. Further analysis of the three immunogenic regions identified within IFNα and termed R1, R2 and R3, was conducted using a time-course T-cell assay. This assay was performed using PBMCs isolated from blood donated by 20 healthy individuals (selected to cover >80% of common HLA-DR alleles) and also from 20 patients with chronic HCV infection previously treated with IFNα2b (IntronA®) according to NICE guidelines (patient studies were conducted under collaboration with Dr G. Alexander, Addenbrooke's Hospital, Cambridge, UK). Immunogenic epitopes R1, R2 and R3 were tested as synthetic peptides as the immunoactive properties of the intact IFNα proteins are not compatible with this assay. In these assays, bulk cultures of $2-4\times10^6$ PBMC/well of a 24 well plate were incubated for 6 to 9 days with peptides spanning the immunogenic regions (see Table 3). Proliferation was assessed at various time points by gently resuspending the bulk cultures and removing samples of PBMC that were then incubated in triplicate wells of U-bottomed 96 well plate with 1 μCi/well tritiated thymidine for 18 hours before harvesting onto glass fibre filter mats using a Tomtec Mach III plate harvester and cpm values determined by scintillation counting using a Wallac Microplate Beta counter.

TABLE 3

Sequences of Peptides Used in:
Time-Course Assays

| Epitope region | Wild type sequence |
|---|---|
| R1 | QMRRISLFSCLKDRHDFGF (SEQ ID NO: 41) |
| R2 | EMIQQIFNLFSTKDSSAAWDETLLDKFY (SEQ ID NO: 42) |
| R3 | TPLMKEDSILAVRKYFQRITLYLKEKKYSPCAW (SEQ ID NO: 43) |

| Epitope region | Modified sequence* |
|---|---|
| R1 | QMRRQSLFSCLKDRHDFGP (SEQ ID NO: 44) |
| R2 | EMTQQIANLFSTKDSSAAHDETLLDKFY (SEQ ID NO: 45) |
| R3 | TPLMKEDSRLAVRKYFQRITNYLKEKKYSPCAW (SEQ ID NO: 46) |

*Amino acid substitutions constituting the modified sequences are shown in bold.

Figure 4A:
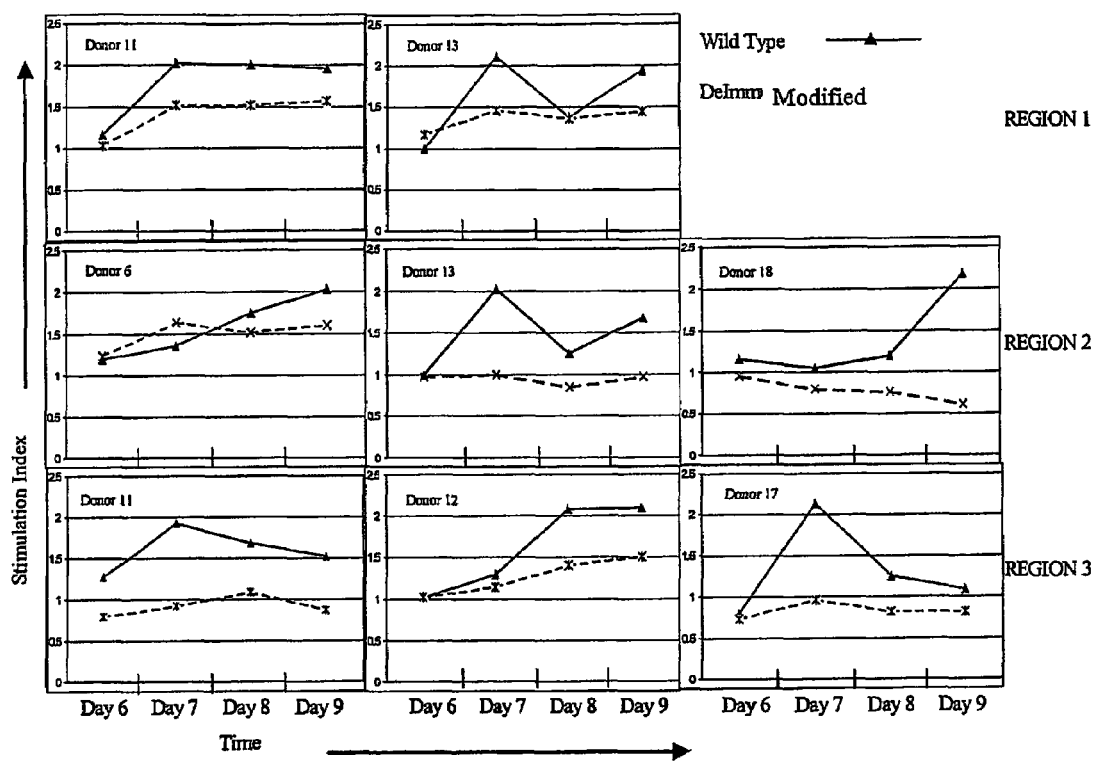
Figure 4B:
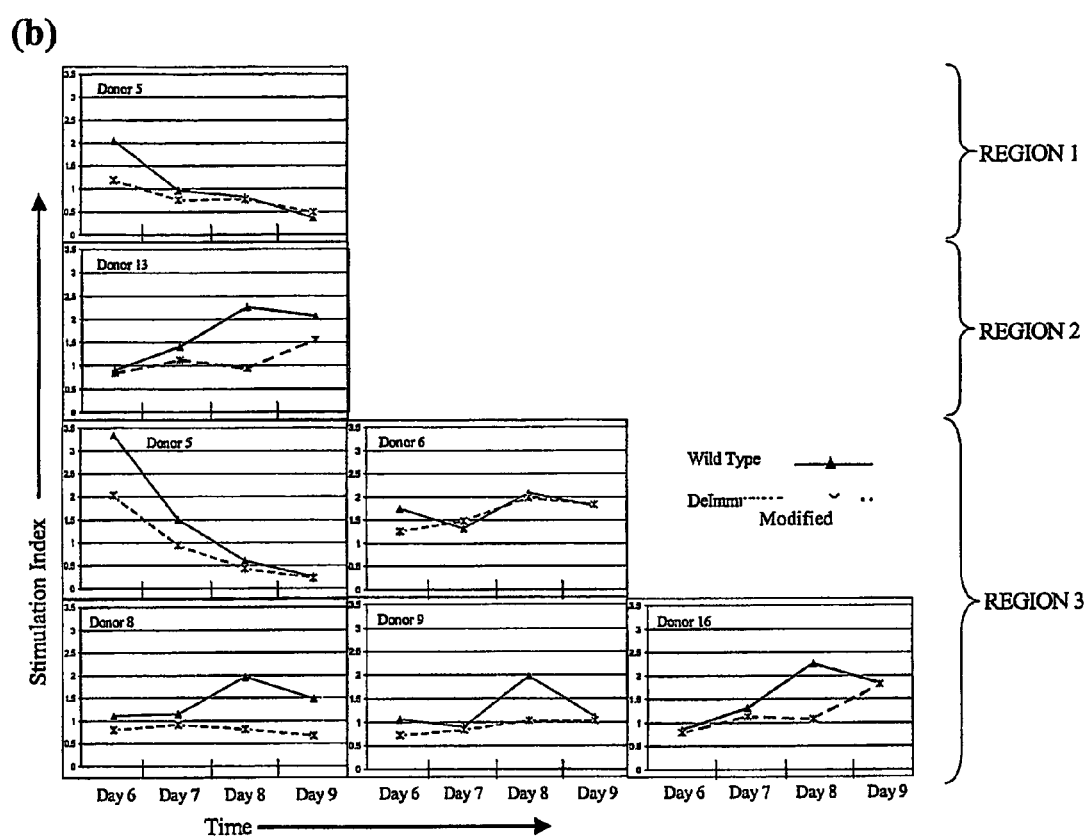
Figure 4C:
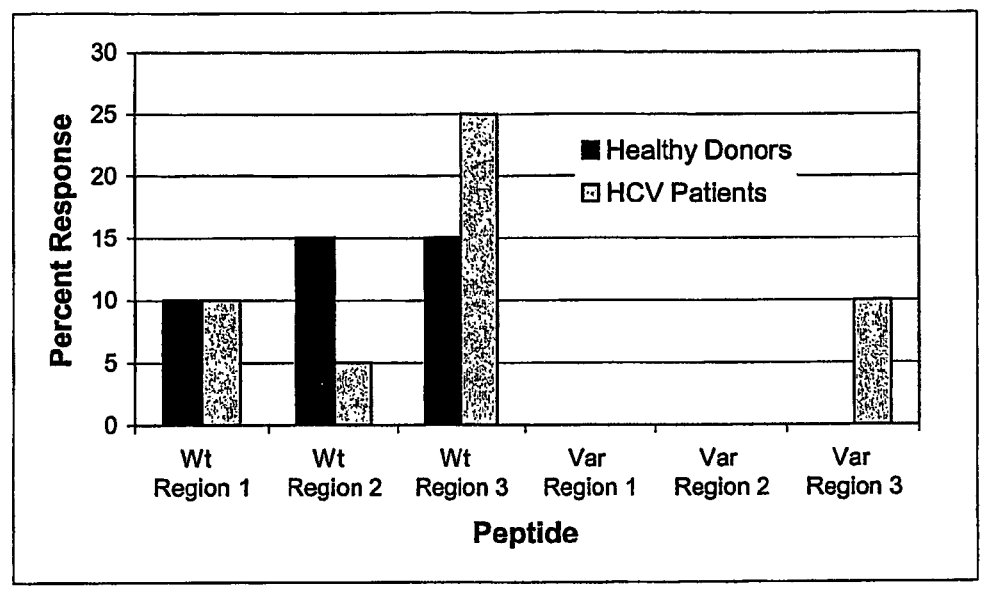

FIG. 4a shows all positive responses (SI>2) by healthy individuals to stimulation with peptides spanning immunogenic regions 1, 2 and 3. Modified peptides failed to induce proliferation in any healthy individuals whereas positive responses to wild type peptides were observed in six donors (FIG. 4a). HCV patients were also found to respond to wild type peptides of all three regions whereas for the modified peptides they only responded to Region 3 (FIG. 4b). Analysis of the frequency of responses to peptides showed that Regions 2 and 3 appeared to induce the most frequent proliferation, in 15% of the healthy donors tested (FIG. 4c), whereas in HCV patients Region 3 induced the highest frequency of responses (25%) followed by Region 1 (10%) and then Region 2 (5%) (FIG. 4c).

From this and other data, Region 3 is considered to contain an immunodominant T-cell epitope since the results from the T-cell epitope mapping show that peptides derived from Region 3 also induce proliferation with the highest frequency in healthy donors [WO 02/085941]. For healthy individuals, responses to the Region 1 peptide were observed on day 7 (FIG. 4a, donor 11 and donor 13), whereas proliferation was detected on day 6 in the only HCV patient T-cell response. The Region 2 peptide tended to induce proliferation on day 9 in healthy donors (FIG. 4a, donor 6 and donor 18) whereas the only HCV patient T-cell response was observed on day 8 (FIG. 4c, donor 13). Unlike Region 1 and 2 responses, the Region 3 peptide induced a more rapid response in healthy individuals than in HCV patients with proliferation observed on days 7 and 8, respectively.

Example 9

Scanning T Cell Assays of IFNα Immunogenic Region 3

Data from scanning T-cell assays conducted on immunogenic Region 3 were also included to further refine the mutein design process. T-cell assays were conducted using PBMC from 13 donor samples the majority of which where predetermined to be responsive to at least the WT peptide sequence of interest. A family of 8 synthetic peptides were produced spanning residues T108-W140 of IFNα. The family of peptides contained the WT sequence and 7 different substituted sequences as identified in Table 4. All assays were conducted in triplicate. The mean SI across the 13 donor samples was determined.

TABLE 4

Mutation Scanning T-cell assays of IFNα immunogenic region 3

| | $I^{116}$ | $L^{117}$ | $V^{119}$ | $Y^{122}$ | $F^{123}$ | $I^{126}$ | $L^{128}$ |
|---|---|---|---|---|---|---|---|
| Substitution | S | A | A | H | H | A | A |
| Mean SI* | 1.58 | 1.53 | 2.46 | — | 1.02 | 1.09 | 1.82 |
| Frequency SI > 1.95 | 15% | 15% | 15% | — | 0% | 15% | 23% |

*T-cell assays were done with peptides spanning IFNα residues T108-W140. Wild type peptide produced an average SI of 2.12 with a 15% frequency of responses.

Alanine was used as the scanning amino acid, except where activity data was already available to guide the choice (Y122 was not scanned since mutants were not active). F123H was found to be the most effective single mutation in reducing the overall T cell response with the SI being consistently less than wild-type over a panel of 13 donors, however F123 could not be mutated to recover sufficient activity. Several of the changes gave an equivalent frequency of positive response to WT (Table 4) but they did not respond to the same subset of donors, although there was some overlap. The mean SI of the mutants were generally lower than WT peptide, even for L128A which gave an increased frequency of positive responses, although V119A gave consistently higher SI over the donor set but the frequency of positive responses was similar to WT. Alternative combinations of region 3 muteins were tested using immunogenicity assay. Nine peptides were synthesised spanning Region 3, containing each combination of amino acids, and re-tested in the T-cell proliferation assay (Table 5).

TABLE 5

Immunogenicity of Region 3 muteins

| Region 3 Mutation | Mean SI[#] (frequency SI > 1.95) |
|---|---|
| WT | 1.43 (15%) |
| I116R + L128N | 1.13 |
| I116R + L128H | 1.21 |
| I116R + L128R | 1.17 |
| I116N + L128N | 1.15 |
| I116N + L128H | 1.14 |

TABLE 5-continued

Immunogenicity of Region 3 muteins

| Region 3 Mutation | Mean SI[#] (frequency SI > 1.95) |
|---|---|
| I116N + L128R | 1.21 (5%) |
| I116T + L128N | 1.10 |
| I116T + L128H | 1.08 |
| I116T + L128R | 1.07 |

[#]T-cell assays were done with peptides spanning IFNα residues T108-W140, containing the Region 3 mutations indicated in the left hand column 15% of donors responded to the WT peptide with an SI>1.95. The mean SI for the WT peptide over all donor samples was 1.43. All combinations of changes gave mean SI over a panel of 20 donors that were less than WT peptide, however the peptide containing I116N+L128R did give a positive response (SI>1.95) in one donor.

The invention claimed is:

1. A modified IFNα2 molecule represented by SEQ ID NO: 25.

* * * * *

SEQUENCE LISTING

```
<160> NUMBER OF SEQ ID NOS: 46

<210> SEQ ID NO 1
<211> LENGTH: 396
<212> TYPE: PRT
<213> ORGANISM: Artificial Sequence
<220> FEATURE:
<223> OTHER INFORMATION: human interferon alpha fusion protein

<400> SEQUENCE: 1

Glu Pro Lys Ser Ser Asp Lys Thr His Thr Cys Pro Pro Cys Pro Ala
 1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
    65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Tyr Ser
            180                 185                 190

Lys Leu Thr Val Asp Lys Ser Arg Trp Gln Gln Gly Asn Val Phe Ser
```

```
                195                 200                 205
Cys Ser Val Met His Glu Ala Leu His Asn His Tyr Thr Gln Lys Ser
    210                 215                 220

Leu Ser Leu Ser Pro Gly Lys Cys Asp Leu Pro Gln Thr His Ser Leu
225                 230                 235                 240

Gly Ser Arg Arg Thr Leu Met Leu Leu Ala Gln Met Arg Arg Ile Ser
                245                 250                 255

Leu Phe Ser Cys Leu Lys Asp Arg His Asp Phe Gly Phe Pro Gln Glu
            260                 265                 270

Glu Phe Gly Asn Gln Phe Gln Lys Ala Glu Thr Ile Pro Val Leu His
        275                 280                 285

Glu Met Ile Gln Gln Ile Phe Asn Leu Phe Ser Thr Lys Asp Ser Ser
    290                 295                 300

Ala Ala His Asp Glu Thr Leu Leu Asp Lys Phe Tyr Thr Glu Leu Tyr
305                 310                 315                 320

Gln Gln Leu Asn Asp Leu Glu Ala Cys Val Ile Gln Gly Val Gly Val
                325                 330                 335

Thr Glu Thr Pro Leu Met Lys Glu Asp Ser Ile Leu Ala Val Arg Lys
            340                 345                 350

Tyr Phe Gln Arg Ile Thr Leu Tyr Leu Lys Glu Lys Lys Tyr Ser Pro
        355                 360                 365

Cys Ala Trp Glu Val Val Arg Ala Glu Ile Met Arg Ser Phe Ser Leu
    370                 375                 380

Ser Thr Asn Leu Gln Glu Ser Leu Arg Ser Lys Glu
385                 390                 395

<210> SEQ ID NO 2
<211> LENGTH: 411
<212> TYPE: PRT
<213> ORGANISM: Artificial Sequence
<220> FEATURE:
<223> OTHER INFORMATION: human interferon alpha mutant fusion protein

<400> SEQUENCE: 2

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
```

```
                    165                 170                 175
Lys Thr Thr Pro Pro Val Leu Asp Ser Asp Gly Ser Phe Phe Tyr Ser
                180                 185                 190

Lys Leu Thr Val Asp Lys Ser Arg Trp Gln Gln Gly Asn Val Phe Ser
                195                 200                 205

Cys Ser Val Met His Glu Ala Leu His Asn His Tyr Thr Gln Lys Ser
                210                 215                 220

Leu Ser Leu Ser Pro Gly Ala Gly Gly Gly Ser Gly Gly Gly Gly
225                 230                 235                 240

Ser Gly Gly Gly Ser Gly Cys Asp Leu Pro Gln Thr His Ser Leu Gly
                245                 250                 255

Ser Arg Arg Thr Leu Met Leu Leu Ala Gln Met Arg Arg Gln Ser Leu
                260                 265                 270

Phe Ser Cys Leu Lys Asp Arg His Asp Phe Gly Phe Pro Gln Glu Glu
                275                 280                 285

Phe Gly Asn Gln Phe Gln Lys Ala Glu Thr Ile Pro Val Leu His Glu
                290                 295                 300

Met Thr Gln Gln Ile Ala Asn Leu Phe Ser Thr Lys Asp Ser Ser Ala
305                 310                 315                 320

Ala His Asp Glu Thr Leu Leu Asp Lys Phe Tyr Thr Glu Leu Tyr Gln
                325                 330                 335

Gln Leu Asn Asp Leu Glu Ala Cys Val Ile Gln Gly Val Gly Val Thr
                340                 345                 350

Glu Thr Pro Leu Met Lys Glu Asp Ser Arg Leu Ala Val Arg Lys Tyr
                355                 360                 365

Phe Gln Arg Ile Thr Asn Tyr Leu Lys Glu Lys Tyr Ser Pro Cys
                370                 375                 380

Ala Trp Glu Val Val Arg Ala Glu Ile Met Arg Ser Phe Ser Leu Ser
385                 390                 395                 400

Thr Asn Leu Gln Glu Ser Leu Arg Ser Lys Glu
                405                 410

<210> SEQ ID NO 3
<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 3

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
```

```
                115                 120                 125
Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys Cys Asp Leu Pro Gln Thr His Ser Leu
225                 230                 235                 240

Gly Ser Arg Arg Thr Leu Met Leu Leu Ala Gln Met Arg Arg Gln Ser
                245                 250                 255

Leu Phe Ser Cys Leu Lys Asp Arg His Asp Phe Gly Phe Pro Gln Glu
            260                 265                 270

Glu Phe Gly Asn Gln Phe Gln Lys Ala Glu Thr Ile Pro Val Leu His
        275                 280                 285

Glu Met Thr Gln Gln Ile Ala Asn Leu Phe Ser Thr Lys Asp Ser Ser
    290                 295                 300

Ala Ala His Asp Glu Thr Leu Leu Asp Lys Phe Tyr Thr Glu Leu Tyr
305                 310                 315                 320

Gln Gln Leu Asn Asp Leu Glu Ala Cys Val Ile Gln Gly Val Gly Val
                325                 330                 335

Thr Glu Thr Pro Leu Met Lys Glu Asp Ser Arg Leu Ala Val Arg Lys
            340                 345                 350

Tyr Phe Gln Arg Ile Thr Asn Tyr Leu Lys Glu Lys Lys Tyr Ser Pro
        355                 360                 365

Cys Ala Trp Glu Val Val Arg Ala Glu Ile Met Arg Ser Phe Ser Leu
    370                 375                 380

Ser Thr Asn Leu Gln Glu Ser Leu Arg Ser Lys Glu
385                 390                 395

<210> SEQ ID NO 4
<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 4

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
```

```
                    85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Arg Glu Glu Met Thr
    130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Tyr Ser
            180                 185                 190
Lys Leu Thr Val Asp Lys Ser Arg Trp Gln Gln Gly Asn Val Phe Ser
        195                 200                 205
Cys Ser Val Met His Glu Ala Leu His Asn His Tyr Thr Gln Lys Ser
    210                 215                 220
Leu Ser Leu Ser Pro Gly Lys Cys Asp Leu Pro Gln Thr His Ser Leu
225                 230                 235                 240
Gly Ser Arg Arg Thr Leu Met Leu Leu Ala Gln Met Arg Arg Gln Ser
                245                 250                 255
Leu Phe Ser Cys Leu Lys Asp Arg His Asp Phe Gly Phe Pro Gln Glu
            260                 265                 270
Glu Phe Gly Asn Gln Phe Gln Lys Ala Glu Thr Ile Pro Val Leu His
        275                 280                 285
Glu Met Ile Gln Gln Ile Phe Asn Leu Phe Ser Thr Lys Asp Ser Ser
    290                 295                 300
Ala Ala His Asp Glu Thr Leu Leu Asp Lys Phe Tyr Thr Glu Leu Tyr
305                 310                 315                 320
Gln Gln Leu Asn Asp Leu Glu Ala Cys Val Ile Gln Gly Val Gly Val
                325                 330                 335
Thr Glu Thr Pro Leu Met Lys Glu Asp Ser Ile Leu Ala Val Arg Lys
            340                 345                 350
Tyr Phe Gln Arg Ile Thr Leu Tyr Leu Lys Glu Lys Lys Tyr Ser Pro
        355                 360                 365
Cys Ala Trp Glu Val Val Arg Ala Glu Ile Met Arg Ser Phe Ser Leu
    370                 375                 380
Ser Thr Asn Leu Gln Glu Ser Leu Arg Ser Lys Glu
385                 390                 395

<210> SEQ ID NO 5
<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 5

Glu Pro Lys Ser Ser Asp Lys Thr His Thr Cys Pro Pro Cys Pro Ala
 1               5                  10                  15
Pro Glu Leu Leu Gly Gly Pro Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
```

```
                50                  55                  60
Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                     85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Tyr Ser
                180                 185                 190

Lys Leu Thr Val Asp Lys Ser Arg Trp Gln Gln Gly Asn Val Phe Ser
                195                 200                 205

Cys Ser Val Met His Glu Ala Leu His Asn His Tyr Thr Gln Lys Ser
210                 215                 220

Leu Ser Leu Ser Pro Gly Lys Cys Asp Leu Pro Gln Thr His Ser Leu
225                 230                 235                 240

Gly Ser Arg Arg Thr Leu Met Leu Leu Ala Gln Met Arg Arg Ile Ser
                245                 250                 255

Leu Phe Ser Cys Leu Lys Asp Arg His Asp Phe Gly Phe Pro Gln Glu
                260                 265                 270

Glu Phe Gly Asn Gln Phe Gln Lys Ala Glu Thr Ile Pro Val Leu His
                275                 280                 285

Glu Met Thr Gln Gln Ile Ala Asn Leu Phe Ser Thr Lys Asp Ser Ser
                290                 295                 300

Ala Ala His Asp Glu Thr Leu Leu Asp Lys Phe Tyr Thr Glu Leu Tyr
305                 310                 315                 320

Gln Gln Leu Asn Asp Leu Glu Ala Cys Val Ile Gln Gly Val Gly Val
                325                 330                 335

Thr Glu Thr Pro Leu Met Lys Glu Asp Ser Thr Leu Ala Val Arg Lys
                340                 345                 350

Tyr Phe Gln Arg Ile Thr Asn Tyr Leu Lys Glu Lys Lys Tyr Ser Pro
                355                 360                 365

Cys Ala Trp Glu Val Val Arg Ala Glu Ile Met Arg Ser Phe Ser Leu
370                 375                 380

Ser Thr Asn Leu Gln Glu Ser Leu Arg Ser Lys Glu
385                 390                 395

<210> SEQ ID NO 6
<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 6

Glu Pro Lys Ser Ser Asp Lys Thr His Thr Cys Pro Pro Cys Pro Ala
 1               5                   10                  15

Pro Glu Leu Leu Gly Gly Pro Ser Val Phe Leu Phe Pro Pro Lys Pro
```

```
                    20                  25                  30
Lys Asp Thr Leu Met Ile Ser Arg Thr Pro Glu Val Thr Cys Val Val
                35                  40                  45
Val Asp Val Ser His Glu Asp Pro Glu Val Lys Phe Asn Trp Tyr Val
            50                  55                  60
Asp Gly Val Glu Val His Asn Ala Lys Thr Lys Pro Arg Glu Glu Gln
65                  70                  75                  80
Tyr Asn Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Arg Glu Glu Met Thr
    130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Tyr Ser
            180                 185                 190
Lys Leu Thr Val Asp Lys Ser Arg Trp Gln Gln Gly Asn Val Phe Ser
        195                 200                 205
Cys Ser Val Met His Glu Ala Leu His Asn His Tyr Thr Gln Lys Ser
    210                 215                 220
Leu Ser Leu Ser Pro Gly Lys Cys Asp Leu Pro Gln Thr His Ser Leu
225                 230                 235                 240
Gly Ser Arg Arg Thr Leu Met Leu Leu Ala Gln Met Arg Arg Ile Ser
                245                 250                 255
Leu Phe Ser Cys Leu Lys Asp Arg His Asp Phe Gly Phe Pro Gln Glu
            260                 265                 270
Glu Phe Gly Asn Gln Phe Gln Lys Ala Glu Thr Ile Pro Val Leu His
        275                 280                 285
Glu Met Thr Gln Gln Ile Ala Asn Leu Phe Ser Thr Lys Asp Ser Ser
    290                 295                 300
Ala Ala His Asp Glu Thr Leu Leu Asp Lys Phe Tyr Thr Glu Leu Tyr
305                 310                 315                 320
Gln Gln Leu Asn Asp Leu Glu Ala Cys Val Ile Gln Gly Val Gly Val
                325                 330                 335
Thr Glu Thr Pro Leu Met Lys Glu Asp Ser Arg Leu Ala Val Arg Lys
            340                 345                 350
Tyr Phe Gln Arg Ile Thr Asn Tyr Leu Lys Glu Lys Lys Tyr Ser Pro
        355                 360                 365
Cys Ala Trp Glu Val Val Arg Ala Glu Ile Met Arg Ser Phe Ser Leu
    370                 375                 380
Ser Thr Asn Leu Gln Glu Ser Leu Arg Ser Lys Glu
385                 390                 395

<210> SEQ ID NO 7
<211> LENGTH: 396
<212> TYPE: PRT
<213> ORGANISM: Artificial Sequence
<220> FEATURE:
<223> OTHER INFORMATION: human interferon alpha mutant fusion protein
```

<400> SEQUENCE: 7

```
Glu Pro Lys Ser Ser Asp Lys Thr His Thr Cys Pro Pro Cys Pro Ala
 1               5                  10                  15
Pro Glu Leu Leu Gly Gly Pro Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
    50                  55                  60
Asp Gly Val Glu Val His Asn Ala Lys Thr Lys Pro Arg Glu Glu Gln
65                  70                  75                  80
Tyr Asn Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Arg Glu Glu Met Thr
    130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Tyr Ser
            180                 185                 190
Lys Leu Thr Val Asp Lys Ser Arg Trp Gln Gln Gly Asn Val Phe Ser
        195                 200                 205
Cys Ser Val Met His Glu Ala Leu His Asn His Tyr Thr Gln Lys Ser
    210                 215                 220
Leu Ser Leu Ser Pro Gly Lys Cys Asp Leu Pro Gln Thr His Ser Leu
225                 230                 235                 240
Gly Ser Arg Arg Thr Leu Met Leu Leu Ala Gln Met Arg Arg Ile Ser
                245                 250                 255
Leu Phe Ser Cys Leu Lys Asp Arg His Asp Phe Gly Phe Pro Gln Glu
            260                 265                 270
Glu Phe Gly Asn Gln Phe Gln Lys Ala Glu Thr Ile Pro Val Leu His
        275                 280                 285
Glu Met Thr Gln Gln Ile Ala Asn Leu Phe Ser Thr Lys Asp Ser Ser
    290                 295                 300
Ala Ala His Asp Glu Thr Leu Leu Asp Lys Phe Tyr Thr Glu Leu Tyr
305                 310                 315                 320
Gln Gln Leu Asn Asp Leu Glu Ala Cys Val Ile Gln Gly Val Gly Val
                325                 330                 335
Thr Glu Thr Pro Leu Met Lys Glu Asp Ser Asn Leu Ala Val Arg Lys
            340                 345                 350
Tyr Phe Gln Arg Ile Thr Asn Tyr Leu Lys Glu Lys Lys Tyr Ser Pro
        355                 360                 365
Cys Ala Trp Glu Val Val Arg Ala Glu Ile Met Arg Ser Phe Ser Leu
    370                 375                 380
Ser Thr Asn Leu Gln Glu Ser Leu Arg Ser Lys Glu
385                 390                 395
```

<210> SEQ ID NO 8

<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 8

```
Glu Pro Lys Ser Ser Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys Cys Asp Leu Pro Gln Thr His Ser Leu
225                 230                 235                 240

Gly Ser Arg Arg Thr Leu Met Leu Leu Ala Gln Met Arg Arg Ile Ser
                245                 250                 255

Leu Phe Ser Cys Leu Lys Asp Arg His Asp Phe Gly Phe Pro Gln Glu
            260                 265                 270

Glu Phe Gly Asn Gln Phe Gln Lys Ala Glu Thr Ile Pro Val Leu His
        275                 280                 285

Glu Met Thr Gln Gln Ile Ala Asn Leu Phe Ser Thr Lys Asp Ser Ser
    290                 295                 300

Ala Ala His Asp Glu Thr Leu Leu Asp Lys Phe Tyr Thr Glu Leu Tyr
305                 310                 315                 320

Gln Gln Leu Asn Asp Leu Glu Ala Cys Val Ile Gln Gly Val Gly Val
                325                 330                 335

Thr Glu Thr Pro Leu Met Lys Glu Asp Ser Ile Leu Ala Val Arg Lys
            340                 345                 350

Tyr Phe Gln Arg Ile Thr Leu Tyr Leu Lys Glu Lys Lys Tyr Ser Pro
        355                 360                 365

Cys Ala Trp Glu Val Val Arg Ala Glu Ile Met Arg Ser Phe Ser Leu
    370                 375                 380
```

Ser Thr Asn Leu Gln Glu Ser Leu Arg Ser Lys Glu
385                 390                 395

<210> SEQ ID NO 9
<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 9

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
210                 215                 220

Leu Ser Leu Ser Pro Gly Lys Cys Asp Leu Pro Gln Thr His Ser Leu
225                 230                 235                 240

Gly Ser Arg Arg Thr Leu Met Leu Leu Ala Gln Met Arg Arg Ile Ser
                245                 250                 255

Leu Phe Ser Cys Leu Lys Asp Arg His Asp Phe Gly Phe Pro Gln Glu
            260                 265                 270

Glu Phe Gly Asn Gln Phe Gln Lys Ala Glu Thr Ile Pro Val Leu Tyr
        275                 280                 285

Glu Met Ile Gln Gln Ile Thr Asn Leu Phe Ser Thr Lys Asp Ser Ser
290                 295                 300

Ala Ala His Asp Glu Thr Leu Leu Asp Lys Phe Tyr Thr Glu Leu Tyr
305                 310                 315                 320

Gln Gln Leu Asn Asp Leu Glu Ala Cys Val Ile Gln Gly Val Gly Val
                325                 330                 335

Thr Glu Thr Pro Leu Met Lys Glu Asp Ser Ile Leu Ala Val Arg Lys
            340                 345                 350

Tyr Phe Gln Arg Ile Thr Leu Tyr Leu Lys Glu Lys Lys Tyr Ser Pro
            355                 360                 365

Cys Ala Trp Glu Val Val Arg Ala Glu Ile Met Arg Ser Phe Ser Leu
        370                 375                 380

Ser Thr Asn Leu Gln Glu Ser Leu Arg Ser Lys Glu
385                 390                 395

<210> SEQ ID NO 10
<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 10

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys Cys Asp Leu Pro Gln Thr His Ser Leu
225                 230                 235                 240

Gly Ser Arg Arg Thr Leu Met Leu Leu Ala Gln Met Arg Arg Ile Ser
                245                 250                 255

Leu Phe Ser Cys Leu Lys Asp Arg His Asp Phe Gly Phe Pro Gln Glu
            260                 265                 270

Glu Phe Gly Asn Gln Phe Gln Lys Ala Glu Thr Ile Pro Val Leu His
        275                 280                 285

Glu Met Ile Gln Gln Ile Phe Asn Leu Phe Ser Thr Lys Asp Ser Ser
    290                 295                 300

Ala Ala His Asp Glu Thr Leu Leu Asp Lys Phe Tyr Thr Glu Leu Tyr
305                 310                 315                 320

-continued

Gln Gln Leu Asn Asp Leu Glu Ala Cys Val Ile Gln Gly Val Gly Val
              325                 330                 335

Thr Glu Thr Pro Leu Met Lys Glu Asp Ser Pro Leu Ala Val Arg Lys
              340                 345                 350

Tyr Phe Gln Arg Ile Thr Leu Tyr Leu Lys Glu Lys Lys Tyr Ser Pro
              355                 360                 365

Cys Ala Trp Glu Val Val Arg Ala Glu Ile Met Arg Ser Phe Ser Leu
              370                 375                 380

Ser Thr Asn Leu Gln Glu Ser Leu Arg Ser Lys Glu
385                 390                 395

<210> SEQ ID NO 11
<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 11

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
              20                  25                  30

Lys Asp Thr Leu Met Ile Ser Arg Thr Pro Glu Val Thr Cys Val Val
              35                  40                  45

Val Asp Val Ser His Glu Asp Pro Glu Val Lys Phe Asn Trp Tyr Val
  50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
              85                  90                  95

Asp Trp Leu Asn Gly Lys Glu Tyr Lys Cys Lys Val Ser Asn Lys Ala
              100                 105                 110

Leu Pro Ala Pro Ile Glu Lys Thr Ile Ser Lys Ala Lys Gly Gln Pro
              115                 120                 125

Arg Glu Pro Gln Val Tyr Thr Leu Pro Pro Ser Arg Glu Glu Met Thr
              130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
              165                 170                 175

Lys Thr Thr Pro Pro Val Leu Asp Ser Asp Gly Ser Phe Phe Tyr Ser
              180                 185                 190

Lys Leu Thr Val Asp Lys Ser Arg Trp Gln Gln Gly Asn Val Phe Ser
              195                 200                 205

Cys Ser Val Met His Glu Ala Leu His Asn His Tyr Thr Gln Lys Ser
              210                 215                 220

Leu Ser Leu Ser Pro Gly Lys Cys Asp Leu Pro Gln Thr His Ser Leu
225                 230                 235                 240

Gly Ser Arg Arg Thr Leu Met Leu Leu Ala Gln Met Arg Arg Ile Ser
              245                 250                 255

Leu Phe Ser Cys Leu Lys Asp Arg His Asp Phe Gly Phe Pro Gln Glu
              260                 265                 270

Glu Phe Gly Asn Gln Phe Gln Lys Ala Glu Thr Ile Pro Val Leu His
              275                 280                 285

```
Glu Met Ile Gln Gln Ile Phe Asn Leu Phe Ser Thr Lys Asp Ser Ser
        290                 295                 300

Ala Ala His Asp Glu Thr Leu Leu Asp Lys Phe Tyr Thr Glu Leu Tyr
305                 310                 315                 320

Gln Gln Leu Asn Asp Leu Glu Ala Cys Val Ile Gln Gly Val Gly Val
                325                 330                 335

Thr Glu Thr Pro Leu Met Lys Glu Asp Ser Thr Leu Ala Val Arg Lys
                340                 345                 350

Tyr Phe Gln Arg Ile Thr Leu Tyr Leu Lys Glu Lys Lys Tyr Ser Pro
            355                 360                 365

Cys Ala Trp Glu Val Val Arg Ala Glu Ile Met Arg Ser Phe Ser Leu
370                 375                 380

Ser Thr Asn Leu Gln Glu Ser Leu Arg Ser Lys Glu
385                 390                 395
```

<210> SEQ ID NO 12
<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 12

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys Cys Asp Leu Pro Gln Thr His Ser Leu
225                 230                 235                 240

Gly Ser Arg Arg Thr Leu Met Leu Leu Ala Gln Met Arg Ile Ser
                245                 250                 255
```

```
Leu Phe Ser Cys Leu Lys Asp Arg His Asp Phe Gly Phe Pro Gln Glu
            260                 265                 270

Glu Phe Gly Asn Gln Phe Gln Lys Ala Glu Thr Ile Pro Val Leu His
            275                 280                 285

Glu Met Ile Gln Gln Ile Phe Asn Leu Phe Ser Thr Lys Asp Ser Ser
            290                 295                 300

Ala Ala His Asp Glu Thr Leu Leu Asp Lys Phe Tyr Thr Glu Leu Tyr
305                 310                 315                 320

Gln Gln Leu Asn Asp Leu Glu Ala Cys Val Ile Gln Gly Val Gly Val
                325                 330                 335

Thr Glu Thr Pro Leu Met Lys Glu Asp Ser Asn Leu Ala Val Arg Lys
            340                 345                 350

Tyr Phe Gln Arg Ile Thr Leu Tyr Leu Lys Glu Lys Lys Tyr Ser Pro
            355                 360                 365

Cys Ala Trp Glu Val Val Arg Ala Glu Ile Met Arg Ser Phe Ser Leu
            370                 375                 380

Ser Thr Asn Leu Gln Glu Ser Leu Arg Ser Lys Glu
385                 390                 395

<210> SEQ ID NO 13
<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 13

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Tyr Ser
            180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
210                 215                 220
```

Leu Ser Leu Ser Pro Gly Lys Cys Asp Leu Pro Gln Thr His Ser Leu
225                 230                 235                 240

Gly Ser Arg Arg Thr Leu Met Leu Leu Ala Gln Met Arg Arg Ile Ser
            245                 250                 255

Leu Phe Ser Cys Leu Lys Asp Arg His Asp Phe Gly Phe Pro Gln Glu
        260                 265                 270

Glu Phe Gly Asn Gln Phe Gln Lys Ala Glu Thr Ile Pro Val Leu His
            275                 280                 285

Glu Met Ile Gln Gln Ile Phe Asn Leu Phe Ser Thr Lys Asp Ser Ser
        290                 295                 300

Ala Ala His Asp Glu Thr Leu Leu Asp Lys Phe Tyr Thr Glu Leu Tyr
305                 310                 315                 320

Gln Gln Leu Asn Asp Leu Glu Ala Cys Val Ile Gln Gly Val Gly Val
                325                 330                 335

Thr Glu Thr Pro Leu Met Lys Glu Asp Ser Ile Leu Ala Val Arg Lys
            340                 345                 350

Tyr Phe Gln Arg Ile Thr Thr Tyr Leu Lys Glu Lys Lys Tyr Ser Pro
        355                 360                 365

Cys Ala Trp Glu Val Val Arg Ala Glu Ile Met Arg Ser Phe Ser Leu
370                 375                 380

Ser Thr Ser Leu Gln Glu Ser Leu Arg Ser Lys Glu
385                 390                 395

<210> SEQ ID NO 14
<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 14

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
        100                 105                 110

Leu Pro Ala Pro Ile Glu Lys Thr Ile Ser Lys Ala Lys Gly Gln Pro
    115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Tyr Ser
        180                 185                 190

```
Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
    210                 215                 220

Leu Ser Leu Ser Pro Gly Lys Cys Asp Leu Pro Gln Thr His Ser Leu
225                 230                 235                 240

Gly Ser Arg Arg Thr Leu Met Leu Leu Ala Gln Met Arg Arg Ile Ser
                245                 250                 255

Leu Phe Ser Cys Leu Lys Asp Arg His Asp Phe Gly Phe Pro Gln Glu
            260                 265                 270

Glu Phe Gly Asn Gln Phe Gln Lys Ala Glu Thr Ile Pro Val Leu His
        275                 280                 285

Glu Met Thr Gln Gln Ile Phe Asn Leu Phe Ser Thr Lys Asp Ser Ser
    290                 295                 300

Ala Ala His Asp Glu Thr Leu Leu Asp Lys Phe Tyr Thr Glu Leu Tyr
305                 310                 315                 320

Gln Gln Leu Asn Asp Leu Glu Ala Cys Val Ile Gln Gly Val Gly Val
                325                 330                 335

Thr Glu Thr Pro Leu Met Lys Glu Asp Ser Ile Leu Ala Val Arg Lys
            340                 345                 350

Tyr Phe Gln Arg Ile Thr Thr Tyr Leu Lys Glu Lys Lys Tyr Ser Pro
        355                 360                 365

Cys Ala Trp Glu Val Val Arg Ala Glu Ile Met Arg Ser Phe Ser Leu
    370                 375                 380

Ser Thr Ser Leu Gln Glu Ser Leu Arg Ser Lys Glu
385                 390                 395

<210> SEQ ID NO 15
<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 15

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160
```

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys Cys Asp Leu Pro Gln Thr His Ser Leu
225                 230                 235                 240

Gly Ser Arg Arg Thr Leu Met Leu Leu Ala Gln Met Arg Arg Ile Ser
                245                 250                 255

Leu Phe Ser Cys Leu Lys Asp Arg His Asp Phe Gly Phe Pro Gln Glu
            260                 265                 270

Glu Phe Gly Asn Gln Phe Gln Lys Ala Glu Thr Ile Pro Val Leu His
        275                 280                 285

Glu Met Thr Gln Gln Ile Phe Asn Leu Phe Ser Thr Lys Asp Ser Ser
    290                 295                 300

Ala Ala Trp Asp Glu Thr Leu Leu Asp Lys Phe Tyr Thr Glu Leu Tyr
305                 310                 315                 320

Gln Gln Leu Asn Asp Leu Glu Ala Cys Val Ile Gln Gly Val Gly Val
                325                 330                 335

Thr Glu Thr Pro Leu Met Lys Glu Asp Ser Ile Leu Ala Val Arg Lys
            340                 345                 350

Tyr Phe Gln Arg Ile Thr Thr Tyr Leu Lys Glu Lys Lys Tyr Ser Pro
        355                 360                 365

Cys Ala Trp Glu Val Val Arg Ala Glu Ile Met Arg Ser Phe Ser Leu
    370                 375                 380

Ser Thr Ser Leu Gln Glu Ser Leu Arg Ser Lys Glu
385                 390                 395

<210> SEQ ID NO 16
<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 16

Glu Pro Lys Ser Ser Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125
```

```
Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys Cys Asp Leu Pro Gln Thr His Ser Leu
225                 230                 235                 240

Gly Ser Arg Arg Thr Leu Met Leu Leu Ala Gln Met Arg Arg Ile Ser
                245                 250                 255

Leu Phe Ser Cys Leu Lys Asp Arg His Asp Phe Gly Phe Pro Gln Glu
            260                 265                 270

Glu Phe Gly Asn Gln Phe Gln Lys Ala Glu Thr Ile Pro Val Leu His
        275                 280                 285

Glu Met Ile Gln Gln Ile Phe Asn Leu Phe Ser Thr Lys Asp Ser Ser
    290                 295                 300

Ala Ala Trp Asp Glu Thr Leu Leu Asp Lys Phe Tyr Thr Glu Leu Tyr
305                 310                 315                 320

Gln Gln Leu Asn Asp Leu Glu Ala Cys Val Ile Gln Gly Val Gly Val
                325                 330                 335

Thr Glu Thr Pro Leu Met Lys Glu Asp Ser Ile Leu Ala Val Arg Lys
            340                 345                 350

Tyr Phe Gln Arg Ile Thr Thr Tyr Leu Lys Glu Lys Lys Tyr Ser Pro
        355                 360                 365

Cys Ala Trp Glu Val Val Arg Ala Glu Ile Met Arg Ser Phe Ser Leu
    370                 375                 380

Ser Thr Asn Leu Gln Glu Ser Leu Arg Ser Lys Glu
385                 390                 395

<210> SEQ ID NO 17
<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 17

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95
```

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
210                 215                 220

Leu Ser Leu Ser Pro Gly Lys Cys Asp Leu Pro Gln Thr His Ser Leu
225                 230                 235                 240

Gly Ser Arg Arg Thr Leu Met Leu Leu Ala Gln Met Arg Arg Ile Ser
                245                 250                 255

Leu Phe Ser Cys Leu Lys Asp Arg His Asp Phe Gly Phe Pro Gln Glu
            260                 265                 270

Glu Phe Gly Asn Gln Phe Gln Lys Ala Glu Thr Ile Pro Val Leu His
        275                 280                 285

Glu Met Ile Gln Gln Ile Phe Asn Leu Phe Ser Thr Lys Asp Ser Ser
290                 295                 300

Ala Ala Trp Asp Glu Thr Leu Leu Asp Lys Phe Tyr Thr Glu Leu Tyr
305                 310                 315                 320

Gln Gln Leu Asn Asp Leu Glu Ala Cys Val Ile Gln Gly Val Gly Val
                325                 330                 335

Thr Glu Thr Pro Leu Met Lys Glu Asp Ser Ile Leu Ala Val Arg Lys
            340                 345                 350

Tyr Phe Gln Arg Ile Thr Ser Tyr Leu Lys Glu Lys Lys Tyr Ser Pro
        355                 360                 365

Cys Ala Trp Glu Val Val Arg Ala Glu Ile Met Arg Ser Phe Ser Leu
    370                 375                 380

Ser Thr Asn Leu Gln Glu Ser Leu Arg Ser Lys Glu
385                 390                 395

<210> SEQ ID NO 18
<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 18

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
        100                 105                 110

Leu Pro Ala Pro Ile Glu Lys Thr Ile Ser Lys Ala Lys Gly Gln Pro
    115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
210                 215                 220

Leu Ser Leu Ser Pro Gly Lys Cys Asp Leu Pro Gln Thr His Ser Leu
225                 230                 235                 240

Gly Ser Arg Arg Thr Leu Met Leu Leu Ala Gln Met Arg Arg Ile Ser
            245                 250                 255

Leu Phe Ser Cys Leu Lys Asp Arg His Asp Phe Gly Phe Pro Gln Glu
        260                 265                 270

Glu Phe Gly Asn Gln Phe Gln Lys Ala Glu Thr Ile Pro Val Leu His
    275                 280                 285

Glu Met Ile Gln Gln Ile Phe Asn Leu Phe Ser Thr Lys Asp Ser Ser
290                 295                 300

Ala Ala Trp Asp Glu Thr Leu Leu Asp Lys Phe Tyr Thr Glu Leu Tyr
305                 310                 315                 320

Gln Gln Leu Asn Asp Leu Glu Ala Cys Val Ile Gln Gly Val Gly Val
                325                 330                 335

Thr Glu Thr Pro Leu Met Lys Glu Asp Ser Ile Leu Ala Val Arg Lys
            340                 345                 350

Tyr Phe Gln Arg Ile Thr Asn Tyr Leu Lys Glu Lys Lys Tyr Ser Pro
        355                 360                 365

Cys Ala Trp Glu Val Val Arg Ala Glu Ile Met Arg Ser Phe Ser Leu
370                 375                 380

Ser Thr Asn Leu Gln Glu Ser Leu Arg Ser Lys Glu
385                 390                 395

<210> SEQ ID NO 19
<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 19

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

```
Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
               100                 105                 110

Leu Pro Ala Pro Ile Glu Lys Thr Ile Ser Lys Ala Lys Gly Gln Pro
               115                 120                 125

Arg Glu Pro Gln Val Tyr Thr Leu Pro Pro Ser Arg Glu Glu Met Thr
       130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
               165                 170                 175

Lys Thr Thr Pro Pro Val Leu Asp Ser Asp Gly Ser Phe Phe Tyr Ser
               180                 185                 190

Lys Leu Thr Val Asp Lys Ser Arg Trp Gln Gln Gly Asn Val Phe Ser
           195                 200                 205

Cys Ser Val Met His Glu Ala Leu His Asn His Tyr Thr Gln Lys Ser
210                 215                 220

Leu Ser Leu Ser Pro Gly Lys Cys Asp Leu Pro Gln Thr His Ser Leu
225                 230                 235                 240

Gly Ser Arg Arg Thr Leu Met Leu Leu Ala Gln Met Arg Arg Ile Ser
               245                 250                 255

Leu Phe Ser Cys Leu Lys Asp Arg His Asp Phe Gly Phe Pro Gln Glu
               260                 265                 270

Glu Phe Gly Asn Gln Phe Gln Lys Ala Glu Thr Ile Pro Val Leu His
       275                 280                 285

Glu Met Ile Gln Gln Ile Phe Asn Leu Phe Ser Thr Lys Asp Ser Ser
       290                 295                 300

Ala Ala Trp Asp Glu Thr Leu Leu Asp Lys Phe Tyr Thr Glu Leu Tyr
305                 310                 315                 320

Gln Gln Leu Asn Asp Leu Glu Ala Cys Val Ile Gln Gly Val Gly Val
               325                 330                 335

Thr Glu Thr Pro Leu Met Lys Glu Asp Ser Ile Leu Ala Val Arg Lys
               340                 345                 350

Tyr Phe Gln Arg Ile Thr His Tyr Leu Lys Glu Lys Lys Tyr Ser Pro
           355                 360                 365

Cys Ala Trp Glu Val Val Arg Ala Glu Ile Met Arg Ser Phe Ser Leu
           370                 375                 380

Ser Thr Asn Leu Gln Glu Ser Leu Arg Ser Lys Glu
385                 390                 395

<210> SEQ ID NO 20
<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 20
```

```
Glu Pro Lys Ser Ser Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
             20                  25                  30

Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
65                   70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
             100                 105                 110

Leu Pro Ala Pro Ile Glu Lys Thr Ile Ser Lys Ala Lys Gly Gln Pro
             115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                 165                 170                 175

Lys Thr Thr Pro Pro Val Leu Asp Ser Asp Gly Ser Phe Phe Tyr Ser
             180                 185                 190

Lys Leu Thr Val Asp Lys Ser Arg Trp Gln Gln Gly Asn Val Phe Ser
             195                 200                 205

Cys Ser Val Met His Glu Ala Leu His Asn His Tyr Thr Gln Lys Ser
210                 215                 220

Leu Ser Leu Ser Pro Gly Lys Cys Asp Leu Pro Gln Thr His Ser Leu
225                 230                 235                 240

Gly Ser Arg Arg Thr Leu Met Leu Leu Ala Gln Met Arg Arg Ile Ser
                 245                 250                 255

Leu Phe Ser Cys Leu Lys Asp Arg His Asp Phe Gly Phe Pro Gln Glu
             260                 265                 270

Glu Phe Gly Asn Gln Phe Gln Lys Ala Glu Thr Ile Pro Val Leu His
             275                 280                 285

Glu Met Ile Gln Gln Ile Phe Asn Leu Phe Ser Thr Lys Asp Ser Ser
             290                 295                 300

Ala Ala Trp Asp Glu Thr Leu Leu Asp Lys Phe Tyr Thr Glu Leu Tyr
305                 310                 315                 320

Gln Gln Leu Asn Asp Leu Glu Ala Cys Val Ile Gln Gly Val Gly Val
                 325                 330                 335

Thr Glu Thr Pro Leu Met Lys Glu Asp Ser Ile Leu Ala Val Arg Lys
             340                 345                 350

Tyr Phe Gln Arg Ile Thr Asp Tyr Leu Lys Glu Lys Lys Tyr Ser Pro
             355                 360                 365

Cys Ala Trp Glu Val Val Arg Ala Glu Ile Met Arg Ser Phe Ser Leu
             370                 375                 380

Ser Thr Asn Leu Gln Glu Ser Leu Arg Ser Lys Glu
385                 390                 395

<210> SEQ ID NO 21
<211> LENGTH: 396
```

<212> TYPE: PRT
<213> ORGANISM: Artificial Sequence
<220> FEATURE:
<223> OTHER INFORMATION: human interferon alpha mutant fusion protein

<400> SEQUENCE: 21

```
Glu Pro Lys Ser Ser Asp Lys Thr His Thr Cys Pro Pro Cys Pro Ala
 1               5                  10                  15
Pro Glu Leu Leu Gly Gly Pro Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
 50                  55                  60
Asp Gly Val Glu Val His Asn Ala Lys Thr Lys Pro Arg Glu Glu Gln
 65                  70                  75                  80
Tyr Asn Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Arg Glu Glu Met Thr
130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Tyr Ser
            180                 185                 190
Lys Leu Thr Val Asp Lys Ser Arg Trp Gln Gln Gly Asn Val Phe Ser
        195                 200                 205
Cys Ser Val Met His Glu Ala Leu His Asn His Tyr Thr Gln Lys Ser
210                 215                 220
Leu Ser Leu Ser Pro Gly Lys Cys Asp Leu Pro Gln Thr His Ser Leu
225                 230                 235                 240
Gly Ser Arg Arg Thr Leu Met Leu Leu Ala Gln Met Arg Arg Ile Ser
                245                 250                 255
Leu Phe Ser Cys Leu Lys Asp Arg His Asp Phe Gly Phe Pro Gln Glu
            260                 265                 270
Glu Phe Gly Asn Gln Phe Gln Lys Ala Glu Thr Ile Pro Val Leu His
        275                 280                 285
Glu Met Ile Gln Gln Ile Phe Asn Leu Phe Ser Thr Lys Asp Ser Ser
290                 295                 300
Ala Ala His Asp Glu Thr Leu Leu Asp Lys Phe Tyr Thr Glu Leu Tyr
305                 310                 315                 320
Gln Gln Leu Asn Asp Leu Glu Ala Cys Val Ile Gln Gly Val Gly Val
                325                 330                 335
Thr Glu Thr Pro Leu Met Lys Glu Asp Ser Ile Leu Ala Val Arg Lys
            340                 345                 350
Tyr Phe Gln Arg Ile Thr Leu Tyr Leu Lys Glu Lys Lys Tyr Ser Pro
        355                 360                 365
Cys Ala Trp Glu Val Val Arg Ala Glu Ile Met Arg Ser Phe Ser Leu
370                 375                 380
```

Ser Thr Asn Leu Gln Glu Ser Leu Arg Ser Lys Glu
385                 390                 395

<210> SEQ ID NO 22
<211> LENGTH: 396
<212> TYPE: PRT
<213> ORGANISM: Artificial Sequence
<220> FEATURE:
<223> OTHER INFORMATION: human interferon alpha mutant fusion protein

<400> SEQUENCE: 22

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys Cys Asp Leu Pro Gln Thr His Ser Leu
225                 230                 235                 240

Gly Ser Arg Arg Thr Leu Met Leu Leu Ala Gln Met Arg Arg Ile Ser
                245                 250                 255

Leu Phe Ser Cys Leu Lys Asp Arg His Asp Phe Gly Phe Pro Gln Glu
            260                 265                 270

Glu Phe Gly Asn Gln Phe Gln Lys Ala Glu Thr Ile Pro Val Leu His
        275                 280                 285

Glu Met Ile Gln Gln Ile Phe Asn Leu Phe Ser Thr Lys Asp Ser Ser
    290                 295                 300

Ala Ala Trp Asp Glu Thr Leu Leu Asp Lys Phe Tyr Thr Glu Leu Asp
305                 310                 315                 320

Gln Gln Leu Asn Asp Leu Glu Ala Cys Val Ile Gln Gly Val Gly Val
                325                 330                 335

Thr Glu Thr Pro Leu Met Lys Glu Asp Ser Ile Leu Ala Val Arg Lys
            340                 345                 350

```
Tyr Phe Gln Arg Ile Thr Leu Tyr Leu Lys Glu Lys Lys Tyr Ser Pro
            355                 360                 365

Cys Ala Trp Glu Val Val Arg Ala Glu Ile Met Arg Ser Phe Ser Leu
370                 375                 380

Ser Thr Asn Leu Gln Glu Ser Leu Arg Ser Lys Glu
385                 390                 395

<210> SEQ ID NO 23
<211> LENGTH: 411
<212> TYPE: PRT
<213> ORGANISM: Artificial Sequence
<220> FEATURE:
<223> OTHER INFORMATION: human interferon alpha fusion protein

<400> SEQUENCE: 23

Glu Pro Lys Ser Ser Asp Lys Thr His Thr Cys Pro Pro Cys Pro Ala
 1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
210                 215                 220

Leu Ser Leu Ser Pro Gly Ala Gly Gly Gly Ser Gly Gly Gly Gly
225                 230                 235                 240

Ser Gly Gly Gly Ser Gly Cys Asp Leu Pro Gln Thr His Ser Leu Gly
                245                 250                 255

Ser Arg Arg Thr Leu Met Leu Leu Ala Gln Met Arg Arg Ile Ser Leu
            260                 265                 270

Phe Ser Cys Leu Lys Asp Arg His Asp Phe Gly Phe Pro Gln Glu Glu
        275                 280                 285

Phe Gly Asn Gln Phe Gln Lys Ala Glu Thr Ile Pro Val Leu His Glu
        290                 295                 300

Met Ile Gln Gln Ile Phe Asn Leu Phe Ser Thr Lys Asp Ser Ser Ala
305                 310                 315                 320
```

```
Ala Trp Asp Glu Thr Leu Leu Asp Lys Phe Tyr Thr Glu Leu Tyr Gln
            325                 330                 335

Gln Leu Asn Asp Leu Glu Ala Cys Val Ile Gln Gly Val Gly Val Thr
            340                 345                 350

Glu Thr Pro Leu Met Lys Glu Asp Ser Ile Leu Ala Val Arg Lys Tyr
            355                 360                 365

Phe Gln Arg Ile Thr Leu Tyr Leu Lys Glu Lys Lys Tyr Ser Pro Cys
370                 375                 380

Ala Trp Glu Val Val Arg Ala Glu Ile Met Arg Ser Phe Ser Leu Ser
385                 390                 395                 400

Thr Asn Leu Gln Glu Ser Leu Arg Ser Lys Glu
            405                 410

<210> SEQ ID NO 24
<211> LENGTH: 165
<212> TYPE: PRT
<213> ORGANISM: Artificial Sequence
<220> FEATURE:
<223> OTHER INFORMATION: human interferon mutant fusion protein variants
<220> FEATURE:
<221> NAME/KEY: VARIANT
<222> LOCATION: 24, 57, 60
<223> OTHER INFORMATION: Xaa=I, Q
      Xaa=H, Y
      Xaa=I, T
<220> FEATURE:
<221> NAME/KEY: VARIANT
<222> LOCATION: 64, 76, 89
<223> OTHER INFORMATION: Xaa=F, T, A
      Xaa=W, H
      Xaa=Y, D
<220> FEATURE:
<221> NAME/KEY: VARIANT
<222> LOCATION: 116, 128, 156
<223> OTHER INFORMATION: Xaa=I, N, T, P, R
      Xaa=L, T, H, D, S, N
      Xaa=N, S

<400> SEQUENCE: 24

Cys Asp Leu Pro Gln Thr His Ser Leu Gly Ser Arg Arg Thr Leu Met
1               5                   10                  15

Leu Leu Ala Gln Met Arg Arg Xaa Ser Leu Phe Ser Cys Leu Lys Asp
            20                  25                  30

Arg His Asp Phe Gly Phe Pro Gln Glu Glu Phe Gly Asn Gln Phe Gln
            35                  40                  45

Lys Ala Glu Thr Ile Pro Val Leu Xaa Glu Met Xaa Gln Gln Ile Xaa
50                  55                  60

Asn Leu Phe Ser Thr Lys Asp Ser Ser Ala Ala Xaa Asp Glu Thr Leu
65                  70                  75                  80

Leu Asp Lys Phe Tyr Thr Glu Leu Xaa Gln Gln Leu Asn Asp Leu Glu
            85                  90                  95

Ala Cys Val Ile Gln Gly Val Gly Val Thr Glu Thr Pro Leu Met Lys
            100                 105                 110

Glu Asp Ser Xaa Leu Ala Val Arg Lys Tyr Phe Gln Arg Ile Thr Xaa
            115                 120                 125

Tyr Leu Lys Glu Lys Lys Tyr Ser Pro Cys Ala Trp Glu Val Val Arg
        130                 135                 140

Ala Glu Ile Met Arg Ser Phe Ser Leu Ser Thr Xaa Leu Gln Glu Ser
145                 150                 155                 160

Leu Arg Ser Lys Glu
            165
```

```
<210> SEQ ID NO 25
<211> LENGTH: 165
<212> TYPE: PRT
<213> ORGANISM: Homo Sapiens
<220> FEATURE:
<223> OTHER INFORMATION: human interferon alpha variant 2b

<400> SEQUENCE: 25

Cys Asp Leu Pro Gln Thr His Ser Leu Gly Ser Arg Arg Thr Leu Met
  1               5                  10                  15

Leu Leu Ala Gln Met Arg Arg Ile Ser Leu Phe Ser Cys Leu Lys Asp
             20                  25                  30

Arg His Asp Phe Gly Phe Pro Gln Glu Glu Phe Gly Asn Gln Phe Gln
         35                  40                  45

Lys Ala Glu Thr Ile Pro Val Leu His Glu Met Ile Gln Gln Ile Phe
     50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 26
<211> LENGTH: 6
<212> TYPE: PRT
<213> ORGANISM: Artificial Sequence
<220> FEATURE:
<223> OTHER INFORMATION: linker peptide

<400> SEQUENCE: 26

Gly Gly Gly Gly Ser Gly
 1               5

<210> SEQ ID NO 27
<211> LENGTH: 11
<212> TYPE: PRT
<213> ORGANISM: Artificial Sequence
<220> FEATURE:
<223> OTHER INFORMATION: linker peptide

<400> SEQUENCE: 27

Gly Gly Gly Gly Ser Gly Gly Gly Gly Ser Gly
 1               5                  10

<210> SEQ ID NO 28
<211> LENGTH: 16
<212> TYPE: PRT
<213> ORGANISM: Artificial Sequence
<220> FEATURE:
<223> OTHER INFORMATION: linker peptide

<400> SEQUENCE: 28
```

```
Gly Gly Gly Gly Ser Gly Gly Gly Ser Gly Gly Gly Ser Gly
  1               5                  10                 15
```

<210> SEQ ID NO 29
<211> LENGTH: 21
<212> TYPE: PRT
<213> ORGANISM: Artificial Sequence
<220> FEATURE:
<223> OTHER INFORMATION: linker peptide

<400> SEQUENCE: 29

```
Gly Gly Gly Gly Ser Gly Gly Gly Gly Ser Gly Gly Gly Gly Ser Gly
  1               5                  10                  15
    Gly Gly Gly Ser Gly
              20
```

<210> SEQ ID NO 30
<211> LENGTH: 16
<212> TYPE: PRT
<213> ORGANISM: Artificial Sequence
<220> FEATURE:
<223> OTHER INFORMATION: linker peptide

<400> SEQUENCE: 30

```
Gly Gly Ser Gly Gly Ser Gly Gly Gly Ser Gly Gly Gly Gly Ser
  1               5                  10                  15
```

<210> SEQ ID NO 31
<211> LENGTH: 15
<212> TYPE: PRT
<213> ORGANISM: Artificial Sequence
<220> FEATURE:
<223> OTHER INFORMATION: linker peptide

<400> SEQUENCE: 31

```
Gly Gly Gly Gly Ser Gly Gly Gly Ser Gly Gly Gly Gly Ser
  1               5                  10                  15
```

<210> SEQ ID NO 32
<211> LENGTH: 5
<212> TYPE: PRT
<213> ORGANISM: Artificial Sequence
<220> FEATURE:
<223> OTHER INFORMATION: linker peptide

<400> SEQUENCE: 32

```
Gly Gly Gly Gly Ser
  1               5
```

<210> SEQ ID NO 33
<211> LENGTH: 10
<212> TYPE: PRT
<213> ORGANISM: Artificial Sequence
<220> FEATURE:
<223> OTHER INFORMATION: linker peptide

<400> SEQUENCE: 33

```
Gly Gly Gly Gly Ser Gly Gly Gly Gly Ser
  1               5                  10
```

<210> SEQ ID NO 34
<211> LENGTH: 4
<212> TYPE: PRT
<213> ORGANISM: Artificial Sequence
<220> FEATURE:
<223> OTHER INFORMATION: linker peptide

<400> SEQUENCE: 34

```
Gly Gly Gly Gly
 1

<210> SEQ ID NO 35
<211> LENGTH: 4
<212> TYPE: PRT
<213> ORGANISM: Artificial Sequence
<220> FEATURE:
<223> OTHER INFORMATION: linker peptide

<400> SEQUENCE: 35

Ala Ala Ala Ala
 1

<210> SEQ ID NO 36
<211> LENGTH: 5
<212> TYPE: PRT
<213> ORGANISM: Artificial Sequence
<220> FEATURE:
<223> OTHER INFORMATION: linker peptide

<400> SEQUENCE: 36

Ala Ala Ala Ala Ala
 1               5

<210> SEQ ID NO 37
<211> LENGTH: 7
<212> TYPE: PRT
<213> ORGANISM: Artificial Sequence
<220> FEATURE:
<223> OTHER INFORMATION: linker peptide

<400> SEQUENCE: 37

Gly Gly Gly Gly Gly Gly Gly
 1               5

<210> SEQ ID NO 38
<211> LENGTH: 5
<212> TYPE: PRT
<213> ORGANISM: Artificial Sequence
<220> FEATURE:
<223> OTHER INFORMATION: linker peptide

<400> SEQUENCE: 38

Gly Gly Pro Gly Gly
 1               5

<210> SEQ ID NO 39
<211> LENGTH: 9
<212> TYPE: PRT
<213> ORGANISM: Artificial Sequence
<220> FEATURE:
<223> OTHER INFORMATION: linker peptide

<400> SEQUENCE: 39

Glu Phe Gly Gly Gly Gly Gly Thr Ala
 1               5

<210> SEQ ID NO 40
<211> LENGTH: 15
<212> TYPE: PRT
<213> ORGANISM: Artificial Sequence
<220> FEATURE:
<223> OTHER INFORMATION: linker peptide

<400> SEQUENCE: 40
```

```
Gly Gly Gly Gly Ser Gly Gly Gly Ser Gly Gly Gly Ser Gly
 1               5                  10                  15
```

<210> SEQ ID NO 41
<211> LENGTH: 19
<212> TYPE: PRT
<213> ORGANISM: Artificial Sequence
<220> FEATURE:
<223> OTHER INFORMATION: peptide antigen

<400> SEQUENCE: 41

```
Gln Met Arg Arg Ile Ser Leu Phe Ser Cys Leu Lys Asp Arg His Asp
 1               5                  10                  15

Phe Gly Phe
```

<210> SEQ ID NO 42
<211> LENGTH: 28
<212> TYPE: PRT
<213> ORGANISM: Artificial Sequence
<220> FEATURE:
<223> OTHER INFORMATION: peptide antigen

<400> SEQUENCE: 42

```
Glu Met Ile Gln Gln Ile Phe Asn Leu Phe Ser Thr Lys Asp Ser Ser
 1               5                  10                  15

Ala Ala Trp Asp Glu Thr Leu Leu Asp Lys Phe Tyr
            20                  25
```

<210> SEQ ID NO 43
<211> LENGTH: 33
<212> TYPE: PRT
<213> ORGANISM: Artificial Sequence
<220> FEATURE:
<223> OTHER INFORMATION: peptide antigen

<400> SEQUENCE: 43

```
Thr Pro Leu Met Lys Glu Asp Ser Ile Leu Ala Val Arg Lys Tyr Phe
 1               5                  10                  15

Gln Arg Ile Thr Leu Tyr Leu Lys Glu Lys Lys Tyr Ser Pro Cys Ala
            20                  25                  30

Trp
```

<210> SEQ ID NO 44
<211> LENGTH: 20
<212> TYPE: PRT
<213> ORGANISM: Artificial Sequence
<220> FEATURE:
<223> OTHER INFORMATION: peptide antigen

<400> SEQUENCE: 44

```
Gln Met Arg Arg Gln Ser Leu Phe Ser Cys Leu Lys Asp Arg His Asp
 1               5                  10                  15

Phe Gly Phe Pro
            20
```

<210> SEQ ID NO 45
<211> LENGTH: 28
<212> TYPE: PRT
<213> ORGANISM: Artificial Sequence
<220> FEATURE:
<223> OTHER INFORMATION: peptide antigen

<400> SEQUENCE: 45

```
Glu Met Thr Gln Gln Ile Ala Asn Leu Phe Ser Thr Lys Asp Ser Ser
```

```
                1               5                    10                   15
Ala Ala His Asp Glu Thr Leu Leu Asp Lys Phe Tyr
                20                   25

<210> SEQ ID NO 46
<211> LENGTH: 28
<212> TYPE: PRT
<213> ORGANISM: Artificial Sequence
<220> FEATURE:
<223> OTHER INFORMATION: peptide antigen

<400> SEQUENCE: 46

Glu Met Thr Gln Gln Ile Ala Asn Leu Phe Ser Thr Lys Asp Ser Ser
 1               5                    10                   15

Ala Ala His Asp Glu Thr Leu Leu Asp Lys Phe Tyr
                20                   25
```